United States Patent
Wang

(10) Patent No.: US 11,835,528 B2
(45) Date of Patent: Dec. 5, 2023

(54) SYSTEM AND METHOD OF ANALYSIS OF A PROTEIN USING LIQUID CHROMATOGRAPHY-MASS SPECTROMETRY

(71) Applicant: Regeneron Pharmaceuticals, Inc., Tarrytown, NY (US)

(72) Inventor: Shunhai Wang, Scarsdale, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 153 days.

(21) Appl. No.: 17/560,626

(22) Filed: Dec. 23, 2021

(65) Prior Publication Data
US 2022/0113317 A1    Apr. 14, 2022

Related U.S. Application Data

(63) Continuation of application No. 16/708,838, filed on Dec. 10, 2019, now Pat. No. 11,249,089.

(60) Provisional application No. 62/778,521, filed on Dec. 12, 2018.

(51) Int. Cl.
| | |
|---|---|
| *G01N 33/68* | (2006.01) |
| *G01N 30/72* | (2006.01) |
| *H01J 49/16* | (2006.01) |
| *G01N 30/02* | (2006.01) |

(52) U.S. Cl.
CPC ..... *G01N 33/6848* (2013.01); *G01N 30/7266* (2013.01); *H01J 49/167* (2013.01); *G01N 2030/027* (2013.01)

(58) Field of Classification Search
CPC ........... G01N 33/6848; G01N 30/7266; G01N 2030/027; H01J 49/167
See application file for complete search history.

(56) References Cited

U.S. PATENT DOCUMENTS

| | | | |
|---|---|---|---|
| 6,544,484 B1 | 4/2003 | Kaufman | |
| 8,759,753 B1* | 6/2014 | Di Bussolo | B01D 15/325 73/1.02 |
| 2007/0102634 A1 | 5/2007 | Frey et al. | |
| 2010/0282962 A1* | 11/2010 | Machuron-Mandard | H01J 49/045 250/288 |
| 2016/0003787 A1 | 1/2016 | Wright | |
| 2016/0329198 A1 | 11/2016 | Badu-Tawiah et al. | |
| 2018/0328898 A1* | 11/2018 | Hioki | H01J 49/0431 |

OTHER PUBLICATIONS

Zhendong and Li, "Chemical Vapor-Assisted Electrospray Ionization for Increasing Analyte Signals in Electrospray Ionization Mass Spectrometry", Analytical Chemistry vol. 85 No. 1, 2013, p. 331-335 (Year: 2013).*

Zhendong Li et al: "Chemical-Vapor-Assisted Electrospray Ionization for Increasing Analyte Signals in Electrospray Ionization Mass Spectrometry," Analytical Chemistry, vol. 86, No. 1, Dec. 23, 2013 (Dec. 23, 2013), pp. 331-335.

(Continued)

*Primary Examiner* — David E Smith
(74) *Attorney, Agent, or Firm* — Kramer Levin Naftalis & Frankel LLP

(57) ABSTRACT

The present disclosure pertains to method and system of characterizing a protein using an electrospray ionization source.

25 Claims, 12 Drawing Sheets

(56) References Cited

OTHER PUBLICATIONS

Zhendong Li Et Al: "Supporting Information," Analytical Chemistry, vol. 86, No. 1, Dec. 23, 2013 (Dec. 23, 2013), Dec. 23, 2013 (Dec. 23, 2013), pp. 1-8, XP055689337, Retrieved from the Internet: URL:https://pubs.acs.org/doi/suppl/10.1021/ac4036263/suppl_file/ac4036263_si_001.pdf [retrieved on Apr. 24, 2020].
Andrea F.G. Gargano et al: "Capillary HILIC-MS: A New Tool for Sensitive Top-Down Proteomics," Analytical Chemistry, vol. 90, No. 11, May 3, 2018 (May 3, 2018), pp. 6601-6609.
Kaspar Stephanie et al: "Technical Note #TN-44 Increasing Peptide Identification Rates for Proteomics Samples by Controlling Peptide Charge States Using CaptiveSpray nanoBooster," Jul. 2013 (Jul. 2013), pp. 1-4, XP055689298, Retrieved from the Internet: URL:https://www.bruker.com/fileadmin/userupload/8-PDF-Docs/eparationsMassSpectrorTletry/Literature/literature/TechNotes/TN-44_CaptiveSpray_nanoBooster_07-2013_eBook.pdf [retrieved on Spr. 24, 2020].
Anastasia Kharlamova et al: "Negative Electrospray Droplet Exposure to Gaseous Bases for the Manipulation of Protein Charge State Distributions," Analytical Chemistry, vol. 83, No. 1, Sep. 12, 2010 (Sep. 12, 2010), pp. 431-437.
Shunhai Wang et al: "Simple Approach for Improved LC-MS Analysis of Protein Biopharmaceuticals via Modification of Desolvation Gas," Analytical Chemistry, vol. 91, No. 4, Jan. 25, 2019 (Jan. 25, 2019), pp. 3156-3162.
European Search Report 19 21 5777, dated Apr. 27, 2020.
Kharlamova et al., "Negative Electrospray Droplet Exposure to Gaseous Bases for the Manipulation of Protein Charge State Distributions", Anal. Chem. vol. 83, No. 1, 2010, p. 431-437 (Year: 2010).
Chen et al, "Manipulation of Charge States of Biopolymer Ions by Atmospheric Pressure Ion/Molecule Reactions Implemented in an Extractive Electrospray Ionization Source", EurJ Mass Spectrom (Chichester), 2007;13(4);273-9 (Year: 2007).
Gargano et al, "Capillary HILIC-MS: A New Tool for Sensitive Top-Down Proteomics", Anal. Chem. Vol. 90 No. 11, 2018, p. 6601-6609 (Year: 2018).

* cited by examiner

SYSTEM AND METHOD OF ANALYSIS OF A PROTEIN USING LIQUID CHROMATOGRAPHY-MASS SPECTROMETRY

CROSS-REFERENCE TO RELATED APPLICATIONS

This application is a continuation of U.S. patent application Ser. No. 16/708,838, filed on Dec. 10, 2019, which claims priority to and the benefit of U.S. Provisional Patent Application No. 62/778,521, filed on Dec. 12, 2018, the content of which is incorporated herein by reference in its entirety.

FIELD

The present invention generally pertains to a method and system of characterizing a protein.

BACKGROUND

Electrospray ionization (ESI)-mass spectrometry (MS) coupled to chromatographic and electrophoretic separation techniques is a key technology in proteomics. It has become an important tool for in-depth characterization of protein biopharmaceuticals in analytical labs to support their developmental and regulatory filings. Protein biopharmaceuticals must meet very high standards of purity and hence it is important to monitor and characterize proteins during different stages of drug development and production.

Liquid chromatography-mass spectrometry (LC-MS)-based analysis of protein biopharmaceuticals could benefit tremendously from improved data quality, which can subsequently lead to improved drug characterization with higher confidence and less ambiguity. To provide characterization of different protein attributes, a wide variety of LC-MS-based assays can be performed, within which peptide mapping analysis and intact mass analysis are most routinely and widely applied. To improve the confidence of the analysis and reduce the ambiguity associated with data interpretation, constant efforts need to be made to improve the data quality from the LC-MS analysis, including using optimized experimental procedures, fine-tuned instrument parameters as well as more advanced mass spectrometers.

From the foregoing it will be appreciated that a need exists for improved methods and systems to improve protein characterization.

SUMMARY

Growth in the development, manufacture and sale of protein-based biopharmaceutical products has led to an increasing demand for methods and systems for characterizing a protein.

Embodiments disclosed herein satisfy the aforementioned demands by providing methods and systems for the characterization of a protein.

The disclosure, at least in part, provides a method of characterizing a protein in a sample, for example: supplying the sample to an inlet of an electrospray ionization source, wherein the electrospray ionization source comprises a container having a cap with an inlet line port and an outlet line port, a sheath gas inlet line, a modified desolvation gas outlet line, an electrospray ionization probe with a sheath gas inlet; generating ions of components of the protein in the sample at an outlet of the electrospray ionization source; and analyzing the ions using a mass spectrometer to identify the components of the protein to characterize the protein.

In some exemplary embodiments, the method of characterizing a protein in a sample can comprise an electrospray ionization source comprising a container having a cap with an inlet line port and an outlet line port and a sheath gas inlet line capable of providing sheath gas to the inlet line port.

In some exemplary embodiments, the method of characterizing a protein in a sample can comprise an electrospray ionization source comprising a container having a cap with an inlet line port and an outlet line port and a modified desolvation gas outlet line capable of connecting the outlet line port to a sheath gas inlet of an electrospray ionization probe.

In some exemplary embodiments, the method of characterizing a protein in a sample can comprise an electrospray ionization source comprising a container surrounded by a second container.

In some exemplary embodiments, the method of characterizing a protein in a sample can comprise an electrospray ionization source with an electrospray ionization probe in a positive polarity mode.

In some exemplary embodiments, the method of characterizing a protein in a sample can comprise an electrospray ionization source with an electrospray ionization probe in a negative polarity mode.

In some exemplary embodiments, the method of characterizing a protein in a sample can comprise conducting an intact mass analysis.

In some exemplary embodiments, the method of characterizing a protein in a sample can comprise conducting a peptide mapping analysis.

In some exemplary embodiments, the method of characterizing a protein in a sample can comprise characterizing an antibody.

In some exemplary embodiments, the method of characterizing a protein in a sample can comprise an electrospray ionization source with a container having an organic solvent.

In some exemplary embodiments, the method of characterizing a protein in a sample can comprise an electrospray ionization source with a container having an organic solvent and an acid.

In some exemplary embodiments, the method of characterizing a protein in a sample can comprise an electrospray ionization source with a container having an organic solvent and a base.

In some exemplary embodiments, the method of characterizing a protein in a sample can comprise an electrospray ionization source with a container having acetonitrile.

In some exemplary embodiments, the method of characterizing a protein in a sample can comprise an electrospray ionization source with a container having triethylamine (TEA).

In some exemplary embodiments, the method of characterizing a protein in a sample can comprise an electrospray ionization source with a container having trifluroacetic acid.

In some exemplary embodiments, the method of characterizing a protein in a sample can comprise an electrospray ionization source having an electrospray ionization probe with an auxiliary gas inlet.

In some exemplary embodiments, the method of characterizing a protein in a sample can comprise an electrospray ionization source having an electrospray ionization probe with an electrospray emitter needle.

In some exemplary embodiments, the method of characterizing a protein in a sample can comprise an electrospray ionization source comprising a container having a cap with an inlet line port and an outlet line port and a sheath gas inlet line capable of providing nitrogen gas to the inlet line port.

In some exemplary embodiments, the method of characterizing a protein in a sample can comprise an electrospray ionization source having an electrospray ionization probe with an auxiliary gas inlet, wherein the auxiliary gas inlet can be capable of being supplied with an auxiliary gas.

In some exemplary embodiments, the method of characterizing a protein in a sample can comprise an electrospray ionization source having an electrospray ionization probe with an auxiliary gas inlet, wherein the auxiliary gas inlet can be capable of being supplied with nitrogen gas.

In some exemplary embodiments, the method of characterizing a protein in a sample can comprise an electrospray ionization source having an electrospray ionization probe including an electrospray emitter needle, a sheath gas flow plumbing, and an auxiliary gas flow plumbing.

In some exemplary embodiments, the method of characterizing a protein in a sample can comprise an electrospray ionization source having an electrospray ionization probe including an electrospray emitter needle, a sheath gas flow plumbing, and auxiliary gas flow plumbing, wherein the electrospray ionization probe can be configured to direct flow in the sheath gas flow plumbing coaxially to the electrospray emitter needle.

In some exemplary embodiments, the method of characterizing a protein in a sample can comprise an electrospray ionization source having an electrospray ionization probe including an electrospray emitter needle, a sheath gas flow plumbing, and an auxiliary gas flow plumbing, wherein the electrospray ionization probe can be configured to direct flow in the auxiliary gas flow plumbing coaxially to the electrospray emitter needle.

In some exemplary embodiments, the method of characterizing a protein in a sample can comprise an electrospray ionization source having an electrospray ionization probe, wherein the electrospray ionization probe can be a heated electrospray ionization probe.

In some exemplary embodiments, the method of characterizing a protein in a sample can comprise an electrospray ionization source having a cap with an inlet line port and a sheath gas inlet line, wherein the sheath gas inlet line can be partially inserted into the inlet line port.

In some exemplary embodiments, the method of characterizing a protein in a sample can comprise an electrospray ionization source having a cap with an outlet line port and a modified desolvation gas outlet line, wherein the a modified desolvation gas outlet line can be partially inserted into to the outlet line port.

In some exemplary embodiments, the method of characterizing a protein in a sample can comprise an electrospray ionization source having a container comprising a cap with an inlet line port and an outlet line port, a sheath gas inlet line, and a modified desolvation gas outlet line, wherein the electrospray ionization source can be configured to allow a flow of a sheath gas from the sheath gas inlet line through the container into the desolvation gas outlet line.

In some exemplary embodiments, the method of characterizing a protein in a sample can comprise an electrospray ionization source having a container comprising a cap with an inlet line port and an outlet line port, a sheath gas inlet line, and a modified desolvation gas outlet line, wherein the electrospray ionization source can be configured to allow a flow of a sheath gas from the sheath gas inlet line through the container having an organic solvent into the desolvation gas outlet line.

In some exemplary embodiments, the method of characterizing a protein in a sample can comprise an electrospray ionization source having a container comprising a cap with an inlet line port and an outlet line port, a sheath gas inlet line, and a modified desolvation gas outlet line, wherein the electrospray ionization source can be configured to allow a flow of a sheath gas from the sheath gas inlet line through the container having an organic solvent and an additional chemical component into the desolvation gas outlet line.

In some exemplary embodiments, the method of characterizing a protein in a sample can comprise an electrospray ionization source capable of providing an electrospray with a solvent flow rate of greater than about 5 µL/min.

In some exemplary embodiments, the method of characterizing a protein in a sample can comprise an electrospray ionization source having a container, wherein the container can be a pressure resistant container.

In some exemplary embodiments, the method of characterizing a protein in a sample can comprise an electrospray ionization source capable of being connected to a liquid chromatographic system.

In some exemplary embodiments, the method of characterizing a protein in a sample can comprise characterizing a digestion product of a protein.

In some exemplary embodiments, the method of characterizing a protein in a sample can comprise analyzing the ions using a mass spectrometer to identify the components of the protein to characterize the protein, wherein the mass spectrometer can be a tandem mass spectrometer.

This disclosure, at least in part, provides a liquid chromatography mass spectrometry system, comprising a liquid chromatography device, an electrospray ionization source having a container having a cap with an inlet line port and an outlet line port, a sheath gas inlet line, a modified desolvation gas outlet line, an electrospray ionization probe and a mass spectrometry device.

In some exemplary embodiments, the liquid chromatography mass spectrometry system can comprise a electrospray ionization source comprising a container having a cap with an inlet line port and an outlet line port and a sheath gas inlet line capable of providing sheath gas to the inlet line port.

In some exemplary embodiments, the liquid chromatography mass spectrometry system can comprise a electrospray ionization source comprising a container having a cap with an inlet line port and an outlet line port and a modified desolvation gas outlet line capable of connecting the outlet line port to a sheath gas inlet of an electrospray ionization probe.

In some exemplary embodiments, the liquid chromatography mass spectrometry system can comprise an electrospray ionization probe that can be capable of being run in a positive polarity mode.

In some exemplary embodiments, the liquid chromatography mass spectrometry system can comprise an electrospray ionization probe that can be capable of being run in a negative polarity mode.

In some exemplary embodiments, the liquid chromatography mass spectrometry system can comprise an electrospray ionization source with a container capable of being filled with an organic solvent.

In some exemplary embodiments, the liquid chromatography mass spectrometry system can comprise a electrospray ionization source with a container capable of being filled with an organic solvent and an additional chemical component, wherein the additional chemical component can include an acid, base, salt, or combinations thereof.

In some exemplary embodiments, the liquid chromatography mass spectrometry system can comprise an electrospray ionization source with a container capable of being filled with an organic solvent and an acid.

In some exemplary embodiments, the liquid chromatography mass spectrometry system can comprise an electrospray ionization source with a container capable of being filled with an organic solvent and a base.

In some exemplary embodiments, the liquid chromatography mass spectrometry system can comprise an electrospray ionization source having an electrospray ionization probe with an auxiliary gas inlet.

In some exemplary embodiments, the liquid chromatography mass spectrometry system can comprise an electrospray ionization source having an electrospray ionization probe with an electrospray emitter needle.

In some exemplary embodiments, the liquid chromatography mass spectrometry system can comprise an electrospray ionization source comprising a container having a cap with an inlet line port and an outlet line port and a sheath gas inlet line capable of providing nitrogen gas to the inlet line port.

In some exemplary embodiments, the liquid chromatography mass spectrometry system can comprise an electrospray ionization source having an electrospray ionization probe with an auxiliary gas inlet, wherein the auxiliary gas inlet can be capable of being supplied with an auxiliary gas.

In some exemplary embodiments, the liquid chromatography mass spectrometry system can comprise an electrospray ionization source having an electrospray ionization probe with an auxiliary gas inlet, wherein the auxiliary gas inlet can be capable of being supplied with nitrogen gas.

In some exemplary embodiments, the liquid chromatography mass spectrometry system can comprise an electrospray ionization source having an electrospray ionization probe including an electrospray emitter needle, a sheath gas flow plumbing, and an auxiliary gas flow plumbing.

In some exemplary embodiments, the liquid chromatography mass spectrometry system can comprise an electrospray ionization source having an electrospray ionization probe including an electrospray emitter needle, a sheath gas flow plumbing, and an auxiliary gas flow plumbing, wherein the electrospray ionization probe can be configured to direct flow in the sheath gas flow plumbing coaxially to the electrospray emitter needle.

In some exemplary embodiments, the liquid chromatography mass spectrometry system can comprise an electrospray ionization source having an electrospray ionization probe including an electrospray emitter needle, a sheath gas flow plumbing, and an auxiliary gas flow plumbing, wherein the electrospray ionization probe can be configured to direct flow in the auxiliary gas flow plumbing coaxially to the electrospray emitter needle.

In some exemplary embodiments, the liquid chromatography mass spectrometry system can comprise an electrospray ionization source having an electrospray ionization probe, wherein the electrospray ionization probe can be a heated electrospray ionization probe.

In some exemplary embodiments, the liquid chromatography mass spectrometry system can comprise an electrospray ionization source having a cap with an inlet line port and a sheath gas inlet line, wherein the sheath gas inlet line can be partially inserted into to the inlet line port.

In some exemplary embodiments, the liquid chromatography mass spectrometry system can comprise an electrospray ionization source having a cap with an outlet line port and a modified desolvation gas outlet line, wherein the modified desolvation gas outlet line can be partially inserted into to the outlet line port.

In some exemplary embodiments, the liquid chromatography mass spectrometry system can comprise an electrospray ionization source having a container comprising a cap with an inlet line port and an outlet line port, a sheath gas inlet line, and a modified desolvation gas outlet line, wherein the electrospray ionization source can be configured to allow a flow of a sheath gas from the sheath gas inlet line through the container into the desolvation gas outlet line.

In some exemplary embodiments the liquid chromatography mass spectrometry system can comprise an electrospray ionization source having a container comprising a cap with an inlet line port and an outlet line port, a sheath gas inlet line, and a modified desolvation gas outlet line, wherein the electrospray ionization source can be configured to allow a flow of a sheath gas from the sheath gas inlet line through the container having an organic solvent into the desolvation gas outlet line.

In some exemplary embodiments, the liquid chromatography mass spectrometry system can comprise an electrospray ionization source having a container comprising a cap with an inlet line port and an outlet line port, a sheath gas inlet line, and a modified desolvation gas outlet line, wherein the electrospray ionization source can be configured to allow a flow of a sheath gas from the sheath gas inlet line through the container having an organic solvent and an additional component into the desolvation gas outlet line.

In some exemplary embodiments, the liquid chromatography mass spectrometry system can comprise electrospray ionization capable of providing an electrospray with a solvent flow rate of greater than about 5 µL/min.

In some exemplary embodiments, the liquid chromatography mass spectrometry system can comprise an electrospray ionization source having a container surrounded by a second container.

In some exemplary embodiments, the liquid chromatography mass spectrometry system can comprise an electrospray ionization source having a container, wherein the container can be a pressure resistant container.

In some exemplary embodiments, the liquid chromatography mass spectrometry system can comprise analyzing the ions using a mass spectrometer to identify the components of the protein to characterize the protein, wherein the mass spectrometer can be a tandem mass spectrometer.

This disclosure, at least in part, provides an electrospray ionization source, comprising a container having a cap with an inlet line port and an outlet line port, a sheath gas inlet, a modified desolvation gas outlet line, and an electrospray ionization probe with a sheath gas inlet.

In some exemplary embodiments, the electrospray ionization source can comprise a container having a cap with an inlet line port and an outlet line port and a sheath gas inlet line capable of providing sheath gas to the inlet line port.

In some exemplary embodiments, the electrospray ionization source can comprise a container having a cap with an inlet line port and an outlet line port and a modified desolvation gas outlet line capable of connecting the outlet line port to a sheath gas inlet of an electrospray ionization probe.

In some exemplary embodiments, the electrospray ionization source can comprise an electrospray ionization probe that can be capable of being run in a positive polarity mode.

In some exemplary embodiments, the electrospray ionization source can comprise an electrospray ionization probe that can be capable of being run in a negative polarity mode.

In some exemplary embodiments, the electrospray ionization source can comprise a container capable of being filled with an organic solvent.

In some exemplary embodiments, the electrospray ionization source can comprise a container capable of being filled with an organic solvent and an acid.

In some exemplary embodiments, the electrospray ionization source can comprise a container capable of being filled with an organic solvent and a base.

In some exemplary embodiments, the electrospray ionization source can comprise an electrospray ionization probe with an auxiliary gas inlet.

In some exemplary embodiments, the electrospray ionization source can comprise an electrospray ionization probe with an electrospray emitter needle.

In some exemplary embodiments, the electrospray ionization source can comprise a container having a cap with an inlet line port and an outlet line port and a sheath gas inlet line capable of providing nitrogen gas to the inlet line port.

In some exemplary embodiments, the electrospray ionization source can comprise an electrospray ionization probe with an auxiliary gas inlet, wherein the auxiliary gas inlet can be capable of being supplied with an auxiliary gas.

In some exemplary embodiments, the electrospray ionization source can comprise an electrospray ionization probe with an auxiliary gas inlet, wherein the auxiliary gas inlet can be capable of being supplied with nitrogen gas.

In some exemplary embodiments, the electrospray ionization source can comprise an electrospray ionization probe including an electrospray emitter needle, a sheath gas flow plumbing, and an auxiliary gas flow plumbing.

In some exemplary embodiments, the electrospray ionization source can comprise an electrospray ionization probe including an electrospray emitter needle, a sheath gas flow plumbing, and an auxiliary gas flow plumbing, wherein the electrospray ionization probe can be configured to direct flow in the sheath gas flow plumbing coaxially to the electrospray emitter needle.

In some exemplary embodiments, the electrospray ionization source can comprise an electrospray ionization probe including an electrospray emitter needle, a sheath gas flow plumbing, and an auxiliary gas flow plumbing, wherein the electrospray ionization probe can be configured to direct flow in the auxiliary gas flow plumbing coaxially to the electrospray emitter needle.

In some exemplary embodiments, the electrospray ionization source can comprise an electrospray ionization probe, wherein the electrospray ionization probe can be a heated electrospray ionization probe.

In some exemplary embodiments, the electrospray ionization source can comprise a container having a cap with an inlet line port and a sheath gas inlet line, wherein the sheath gas inlet line can be partially inserted into to the inlet line port.

In some exemplary embodiments, the electrospray ionization source can comprise an electrospray ionization source having a cap with an outlet line port and a modified desolvation gas outlet line, wherein the modified desolvation gas outlet line can be partially inserted into to the outlet line port.

In some exemplary embodiments, the electrospray ionization source can comprise a container comprising a cap with an inlet line port and an outlet line port, a sheath gas inlet line, and a modified desolvation gas outlet line, wherein the electrospray ionization source can be configured to allow a flow of a sheath gas from the sheath gas inlet line through the container into the desolvation gas outlet line.

In some exemplary embodiments, the electrospray ionization source can comprise a container comprising a cap with an inlet line port and an outlet line port, a sheath gas inlet line, and a modified desolvation gas outlet line, wherein the electrospray ionization source can be configured to allow a flow of a sheath gas from the sheath gas inlet line through the container having an organic solvent into the desolvation gas outlet line.

In some exemplary embodiments, the electrospray ionization source can comprise a container comprising a cap with an inlet line port and an outlet line port, a sheath gas inlet line, and a modified desolvation gas outlet line, wherein the electrospray ionization source can be configured to allow a flow of a sheath gas from the sheath gas inlet line through the container having an organic solvent and an additional component into the desolvation gas outlet line.

In some exemplary embodiments the electrospray ionization source can comprise a container surrounded by a second container.

In some exemplary embodiments, the electrospray ionization source can comprise a container, wherein the container can be a pressure resistant container.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
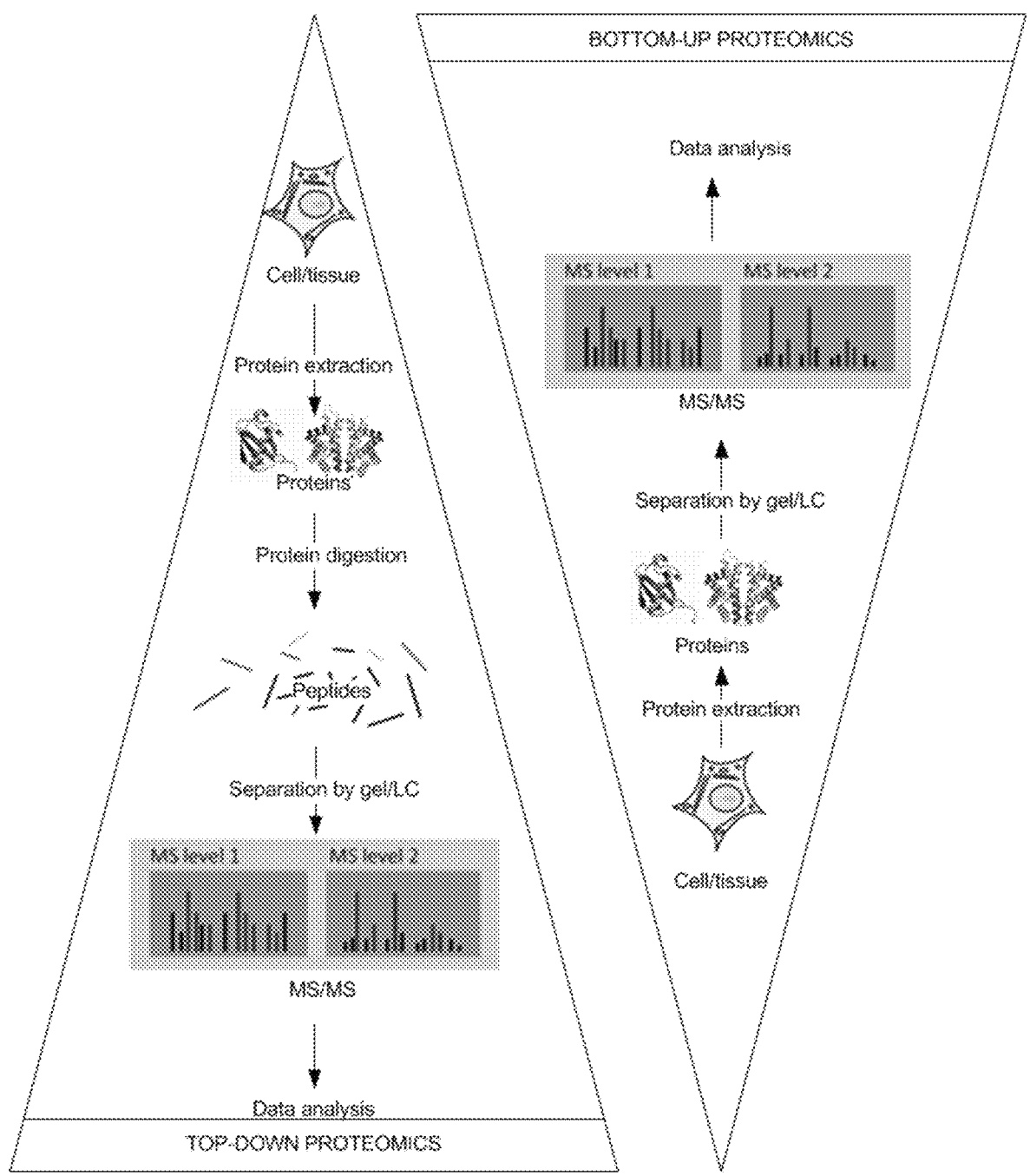
FIG. 1 shows a schematic illustration of the difference between top-down and bottom-up proteomics.

LC-MS based peptide mapping analysis is routinely applied to confirm the primary sequence of protein biopharmaceuticals, where a protein molecule is first hydrolyzed into small peptide fragments using a protease with known specificity (although non-specific protease can also be applied occasionally), and then the amino acid sequence of each peptide fragment is determined by LC-MS/MS analysis taking into consideration of the cDNA predicted sequence and the specificity of the protease used (Dick et al. Journal of chromatography. B, Analytical technologies in the biomedical and life sciences 2009, 877, 230-236; Bongers et al. Journal of pharmaceutical and biomedical analysis 2000, 21, 1099-1128; Mouchahoir and Schiel Analytical and bioanalytical chemistry 2018, 410, 2111-2126). Data from peptide mapping analysis could also be utilized to identify and quantify post-translational modifications, confirm the disulfide bond linkages and even detect amino acid substitution events present at very low levels (<0.1%) (Zeck et al. PloS one 2012, 7, e40328). During peptide mapping analysis of protein biopharmaceuticals, LC-MS is often performed in combination with ultraviolet (UV) detection to generate so-called UV fingerprints, which alone can be used as an identification assay during quality control (QC) and drug release. To effectively separate peptides on a reversed-phase column with good peak shape, trifluoroacetic acid (TFA) is commonly used as a mobile phase modifier due to its excellent ion pairing ability (Shibue, et al. Journal of chromatography. A 2005, 1080, 68-75).

However, TFA is also notoriously known for its ion suppression effects during the electrospray (ESI) process due to the increased surface tension as well as its ability to form ion pairs with analytes in gas phase, thus leading to significantly decreased MS sensitivity (Annesley, T. M. Clinical chemistry 2003, 49, 1041-1044). Over the past two decades, different strategies have been investigated and implemented to alleviate the MS sensitivity loss related to TFA. For example, modifying the TFA-containing mobile phases with acetic acid or propionic acid has demonstrated a significant MS signal enhancement without compromising the chromatography integrity for bioanalysis of some basic compounds (Shou and Naidong. Journal of chromatography. B, Analytical technologies in the biomedical and life sciences 2005, 825, 186-192). Post-column addition of a mixture of propionic acid and isopropanol is another commonly used strategy which does not require the modification of the LC method. However, this setup does require additional pumps, consume large quantity of chemicals and is not suitable for continuous analysis of large sample sets (Apffel et al. Journal of chromatography. A 1995, 712, 177-190). Acid vapor assisted ESI within an enclosed spray chamber is a solution to counteract the signal suppression effects of TFA (Chen et al. Chemical communications 2015, 51, 14758-14760). However, its utility in protein biopharmaceutical characterization has been limited so far, presumably due to the requirement of a special ESI source.

Finally, the advances in reversed-phase column chemistry, particularly the development of charged-surface C18 stationary phases, significantly reduced the dependence of using TFA to achieve good peak shape during peptide mapping analysis (Lauber et al. J. Analytical chemistry 2013, 85, 6936-6944). Replacing TFA with a MS-friendly mobile phase modifier (e.g. formic acid), however, will inevitably reduce the retention of most peptides, rendering some short and hydrophilic peptides undetectable due to co-elution with the solvent front, resulting in decreased sequence coverage. Nevertheless, until those new columns have been routinely and widely adopted in protein biopharmaceutical characterization, TFA-based LC-MS method is still the mainstream in peptide mapping analysis. Considering the limitations of existing methods, an effective and efficient system and method for characterization of proteins was developed as disclosed herein. A simple approach to counteract TFA ion suppression during LC-MS analysis was carried out by modifying the desolvation gas with acid/base vapor and isopropanol.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

Protein biopharmaceuticals are required to show high levels of potency, purity, and low level of structural heterogeneity. Structural heterogeneity often affects the bioactivity and efficacy of a drug. Therefore, characterizing and quantifying the protein and/or the impurities is important in pharmaceutical drug development.

In some exemplary embodiments, the disclosure provides a method for characterizing an impurity in a sample.

As used herein, the term "protein" includes any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides' refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic proteins. Occurrence, impact, and challenges of non-human sialylation," (Biotechnol. Genet. Eng. Rev. (2012) 147-75). In some embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein can be an antibody, a bispecific antibody, a multispecific antibody, antibody fragment, monoclonal antibody, or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment contains sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by a $C_H1$ domain, a hinge, a $C_H2$ domain, and a $C_H3$ domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats, such as, but not limited to triomab, knobs into holes IgG (kih IgG), crossMab, orth-Fab IgG, Dual-variable domains Ig (DVD-Ig), Two-in-one or dual action Fab (DAF), IgG-single-chain Fv (IgG-scFv), or κλ-bodies. The non-IgG-like different formats include Tandem scFvs, Diabody format, Single-chain diabody, tandem diabodies (TandAbs), Dual-affinity retargeting molecule (DART), DART-Fc, nanobodies, or antibodies produced by the dock-and-lock (DNL) method. Fan et al. and Kontermann and Brinkmann present a detailed review on bispecific antibody (Fan et al. "Bispecific antibodies and their applications" J. Hematol. Oncol. (2015) 8:130; Kontermann and Brinkmann. "Bispecific antibodies" Drug Discov. Today (2015) 20: 838-847). The methods of producing BsAbs are not limited to quadroma technology based on the somatic fusion of two different hybridoma cell lines, chemical conjugation, which involves chemical cross-linkers, and genetic approaches utilizing recombinant DNA technology. Examples of bsAbs include those disclosed in the following patent applications, which are hereby incorporated by reference in their entirety: U.S. Pat. No. 8,586,713, filed Jun. 25, 2010; U.S. Pat. Publication No. 2013/0045492, filed Jun. 5, 2012; U.S. Pat. No. 9,657,102, filed Sep. 19, 2013; U.S. Pat. Publication No. 2016/0024147, filed Jul. 24, 2015; U.S. Pat. Publication No. 2018/0112001, filed Sep. 22, 2017; U.S. Pat. Publication No. 2018/0104357, field Sep. 22, 2017; U.S. Pat. Publication No. 2017/0174779, filed Dec. 21, 2016; U.S. Pat. Publication No. 2017/0174781, filed Dec. 21, 2016; U.S. Pat. No. 10,179,819, filed Jul. 29, 2016; and U.S. Pat. Publication No. 2018/0134794, filed Nov. 15, 2017. Low levels of homodimer impurities can be present at several steps during the manufacturing of bispecific antibodies. The detection of such homodimer impurities can be challenging when performed using intact mass analysis due to low abundances of the homodimer impurities and the co-elution of these impurities with main species when carried out using a regular liquid chromatographic method.

As used herein "multispecific antibody" or "Mab" refers to an antibody with binding specificities for at least two different antigens. While such molecules normally will only bind two antigens (i.e. bispecific antibodies, BsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

During many stages of production of biopharmaceuticals, impurities can be formed. Biotechnology-derived impurities can be very difficult to characterize and quantify, because they often are present at very low levels, and because they can represent very complicated species or mixtures of species. It can also be very difficult to obtain an authentic reference standard of the impurity peaks. However, to fully characterize a trace amount of an impurity protein becomes a time consuming, lengthy, and often very expensive process. Often, the impurity can include variants, isoforms, degradation products, product-related impurities, process-related, minor post translational modifications, aggregates, or clipped fragments of the intact recombinant protein.

In some exemplary embodiments, the disclosure provides a method for characterizing a protein in a sample.

As used herein, the term "impurity" can include any undesirable protein present in the biopharmaceutical product. Impurity can include process and product-related impurities. The impurity can further be of known structure, partially characterized, or unidentified. Process-related impurities can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. Product-related impurities (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification (s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S—S linked, oxidized, or altered conjugated forms (e.g., glycosylation, phosphorylation). Modified forms can also include any post-translational modification form. Aggregates include dimers and higher multiples of the desired product. (Q6B Specifications: Test Procedures and Acceptance Criteria for Biotechnological/Biological Products, ICH August 1999, U.S. Dept. of Health and Humans Services).

As used herein, the general term "post-translational modifications" or "PTMs" refer to covalent modifications that polypeptides undergo, either during (co-translational modification) or after (post-translational modification) their ribosomal synthesis. PTMs are generally introduced by specific enzymes or enzyme pathways. Many occur at the site of a specific characteristic protein sequence (e.g., signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (e.g., the conversion of arginine to citrulline by deimination), and deamidation (e.g., the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See http://www.uniprot.org/docs/ptmlist for a more detailed controlled vocabulary of PTMs curated by UniProt.

"Variant protein" or "protein variant", or "variant" as used herein can include a protein that differs from a target protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about ten amino acid modifications, and preferably from about one to about five amino acid modifications compared to the parent. The protein variant sequence herein will preferably possess at least about 80% homology with a parent protein sequence, and most preferably at least about 90% homology, more preferably at least about 95% homology.

Comprehensive characterization of proteins can satisfy safety standards set by regulatory agencies and help to ensure protein drug efficacy. Proteomics approaches are thus important in the biopharmaceutical industry where they aid in the identity confirmation of a protein, monitoring impurities, monitoring protein modifications such as PTMs and protein variants, monitoring degradative events such as oxidation or deamidation, etc. Proteomics approaches can be discriminated by the level at which analysis takes place (See FIG. 1).

"Intact mass analysis" as used herein includes top-down experiments wherein a protein is characterized as an intact protein (See FIG. 1, left panel). Intact mass analysis can reduce sample preparation to a minimum and preserve information that can sometimes get lost in other proteomics strategies, such as the connectivity of multiple PTMs.

Some proteomics experiments rely on digestion of the protein into peptides prior to MS analysis. "Peptide mapping analysis" as used herein includes experiments wherein the protein undergoes digestion followed by separation of the resulting peptides and their analysis, preferably using LC-MS (See FIG. 1, right panel). In some exemplary embodiments, peptide mapping analysis can be applied to confirm the primary sequence of protein biopharmaceuticals, where a protein molecule can be first hydrolyzed into small peptide fragments using a hydrolyzing agent and then the amino acid sequence of each peptide fragment is determined by LC-MS/MS analysis taking into consideration of the cDNA predicted sequence and the specificity of the protease used. Data from peptide mapping analysis could also be utilized to identify and quantify post-translational modifications, confirm the disulfide bond linkages and even detect amino acid substitution events present at very low levels (<0.1%) (Zeck et al. PloS one 2012, 7, e40328). During peptide mapping analysis of protein biopharmaceuticals, LC-MS can be often performed in combination with ultraviolet (UV) detection to generate so-called UV fingerprints, which alone can be used as an identification assay during quality control (QC) and drug release.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion. As used herein, the term "hydrolyzing agent" refers to any one or combination of a large number of different agents that can perform digestion of a protein. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus Saitoi*. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (J. Proteome Research 2013, 12, 1067-1077). One or a combination of hydrolyzing agents can cleave peptide bonds in a protein or polypeptide, in a sequence-specific manner, generating a predictable collection of shorter peptides.

Several approaches are available that can be used to digest a protein. One of the widely accepted methods for digestion of proteins in a sample involves the use of proteases. Many proteases are available and each of them has their own characteristics in terms of specificity, efficiency, and optimum digestion conditions. Proteases refer to both endopeptidases and exopeptidases, as classified based on the ability of the protease to cleave at non-terminal or terminal amino acids within a peptide. Alternatively, proteases also refer to the six distinct classes—aspartic, glutamic, and metalloproteases, cysteine, serine, and threonine proteases, as classified on the mechanism of catalysis. The terms "protease" and "peptidase" are used interchangeably to refer to enzymes which hydrolyze peptide bonds. Proteases can also be classified into specific and non-specific proteases. As used herein, the term "specific protease" refers to a protease with an ability to cleave the peptide substrate at a specific amino acid side chain of a peptide. As used herein, the term "non-specific protease" refers to a protease with a reduced ability to cleave the peptide substrate at a specific amino acid side chain of a peptide. A cleavage preference may be determined based on the ratio of the number of a particular amino acid as the site of cleavage to the total number of cleaved amino acids in the protein sequences The protein can optionally be prepared before characterizing. In some exemplary embodiments, the protein preparation includes a step of protein digestion. In some specific exemplary embodiments, the protein preparation includes a step of protein digestion, wherein the protein digestion can be carried out using trypsin.

In some exemplary embodiments, the protein preparation can include a step for denaturing the protein, reducing the protein, buffering the protein, and/or desalting the sample, before the step of protein digestion. These steps can be accomplished in any suitable manner as desired.

To provide characterization of different protein attributes using either peptide mapping analysis or intact mass analysis, a wide variety of LC-MS based assays can be performed.

As used herein, the term "liquid chromatography" refers to a process in which a chemical mixture carried by a liquid can be separated into components as a result of differential distribution of the chemical entities as they flow around or over a stationary liquid or solid phase. Non-limiting examples of liquid chromatography include reverse phase liquid chromatography, ion-exchange chromatography, size exclusion chromatography, affinity chromatography, and hydrophobic chromatography.

As used herein, the term "mass spectrometer" refers to a device capable of detecting specific molecular species and accurately measuring their masses. The term can be meant to include any molecular detector into which a polypeptide or peptide may be eluted for detection and/or characterization. A mass spectrometer consists of three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends on the application.

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray emitter needle containing the solution and a counter electrode. There are three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus.

As used herein, the term "electrospray ionization source" refers to an electrospray ionization system that can be compatible with a mass spectrometer used for mass analysis of protein. In electrospray ionization, an electrospray emitter needle has its orifice positioned close to the entrance orifice of a spectrometer. A sample, containing the protein of interest, can be pumped through the electrospray emitter needle. An electric potential between the electrospray emitter needle orifice and an orifice leading to the mass analyzer forms a spray ("electrospray") of the solution. The electrospray can be carried out at atmospheric pressure and provides highly charged droplets of the solution. The electrospray ionization source can be configured to operate in any of several atmospheric pressure ionization (API) modes, including electrospray ionization (ESI), heated-electrospray ionization (H-ESI), and atmospheric pressure chemical ionization (APCI), and atmospheric pressure photo-ionization (APPI). The electrospray infusion setup can optionally be automated to carry out sample aspiration, sample dispensing, sample delivery, and/or for spraying the sample. The electrospray ionization probe can produce charged aerosol droplets that contain sample ions. The ESI probe can accommodate liquid flows of 5 µL/min to 1 mL/min without splitting.

The ESI probe can include the ESI sample tube, the electrospray emitter needle, a nozzle, and a manifold. Sample and solvent can enter the ESI probe through the sample tube. The sample tube can be a short section of OD fused-silica tubing that extends from the stainless steel grounding to the end of the ESI needle. The electrospray emitter needle, to which a large negative or positive voltage can be applied, can spray the sample solution into a fine mist of charged droplets. The ESI nozzle can direct the flow of sheath gas and auxiliary gas at the droplets. The ESI manifold can house an ESI nozzle, an electrospray emitter needle, a sheath gas inlet, an auxiliary gas inlet, a sheath gas plumbing, and an auxiliary gas plumbing. The sheath gas plumbing and auxiliary gas plumbing can deliver dry gas to the nozzle. The sheath gas inlet and auxiliary gas inlet in the manifold can be connected to sheath gas inlet line and auxiliary gas inlet line, respectively. Alternatively, the sheath gas inlet and auxiliary gas inlet in the manifold can be connected to modified desolvation gas outlet line and auxiliary gas inlet line, respectively. The connection of gas inlets with the gas inlet lines can be performed using adapter fittings.

The term "nanoelectrospray" or "nanospray" as used herein refers to electrospray ionization at a very low solvent flow rate, typically hundreds of nanoliters per minute of sample solution or lower, often without the use of an external solvent delivery.

As used herein, "mass analyzer" refers to a device that can separate species, that is, atoms, molecules, or clusters, according to their mass. Non-limiting examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

As used herein, "mass-to-charge ratio" or "m/z" is used to denote the dimensionless quantity formed by dividing the mass of an ion in unified atomic mass units by its charge number (regardless of sign). In general, the charge state depends on: the method of ionization (as electrospray ionization, ESI tends to promote multiple ionization, which is not as frequent in MALDI), peptide length (as longer peptides have more groups where additional protons can be attached (basic residues)), peptide sequence (as some amino acids (e.g., Arg or Lys) are more susceptible to ionization than others), the instrument settings, solvent pH, and solvent composition.

As used herein, the term "tandem mass spectrometry" refers to a technique where structural information on sample molecules can be obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or MSn, can be performed by first selecting and isolating a precursor ion ($MS^2$), fragmenting it, isolating a primary fragment ion ($MS^3$), fragmenting it, isolating a secondary fragment ($MS^4$), and so on as long as one can obtain meaningful information or the fragment ion signal is detectable. Tandem MS have been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers.

A tandem-in-space mass spectrometer comprise of an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition.

In tandem-in-time mass spectrometer ions produced in the ion source can be trapped, isolated, fragmented, and m/z separated in the same physical device.

As used herein, the term "quadrupole—Orbitrap hybrid mass spectrometer" refers to a hybrid system made by coupling a quadrupole mass spectrometer to an orbitrap mass analyzer. A tandem in-time experiment using the quadrupole—Orbitrap hybrid mass spectrometer begins with ejection of all ions except those within a selected, narrow m/z range from the quadrupole mass spectrometer. The selected ions can be inserted into orbitrap and fragmented most often by low-energy CID. Fragments within the m/z acceptance range of the trap should remain in the trap, and an MS-MS spectrum can be obtained. Similar hybrid systems can be used for fast protein sequencing, such as, but not limited to QIT-FTICR and Qq-FTICR.

It is understood that the present invention is not limited to any of the aforesaid liquid chromatography, mass spectrometer, and that any liquid chromatography or mass spectrometer can be selected by any suitable means.

Characterization of the Protein

The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited, to sequencing amino acids of the protein fragments, determining protein sequencing, determining protein de novo sequencing, locating post-translational modifications, or identifying post translational modifications, or comparability analysis, or combinations thereof.

As used herein, the term "protein de novo sequencing" refers to a procedure for determination of the amino acid sequence of a peptide without relying on the information gained from other sources. Due to the high level of sensitivity of mass spectrometry, this technique can provide vital information that is often beyond the capabilities of conventional sequencing methods.

As used herein, the term "protein sequence coverage" refers to the percentage of the protein sequence covered by identified peptides. The percent coverage can be calculated by dividing the number of amino acids in all found peptides by the total number of amino acids in the entire protein sequence.

As used herein, the term "database" refers to bioinformatic tools which provide the possibility of searching the uninterpreted MS-MS spectra against all possible sequences in the database(s). Non-limiting examples of such tools are Mascot (http://www.matrixscience.com), Spectrum Mill (http://www.chem.agilent.com), PLGS (http://www.waters.com), PEAKS (http://www.bioinformaticssolutions.com), Proteinpilot (http://download.appliedbiosystems.com//proteinpilot), Phenyx (http://www.phenyx-ms.com), Sorcerer (http://www.sagenresearch.com), OMSSA (http://www.pubchem.ncbi.nlm.nih.gov/omssa/), X!Tandem (http://www.thegpm.org/TANDEM/), Protein Prospector (http://www. http://prospector.ucsf.edu/prospector/mshome.htm), Byonic (https://www.proteinmetrics.com/products/byonic) or Sequest (http://fieldsserippsedu/sequest).

Exemplary Embodiments

Embodiments disclosed herein provide compositions, methods, and systems for the rapid characterization of proteins in a sample.

As used herein, the terms "include," "includes," and "including," are meant to be non-limiting and are understood to mean "comprise," "comprises," and "comprising," respectively.

In some exemplary embodiments, the disclosure provides a liquid chromatography mass spectrometry system, comprising (i) liquid chromatography device, (ii) an electrospray ionization source and (iii) a mass spectrometry device.

Figure 2:
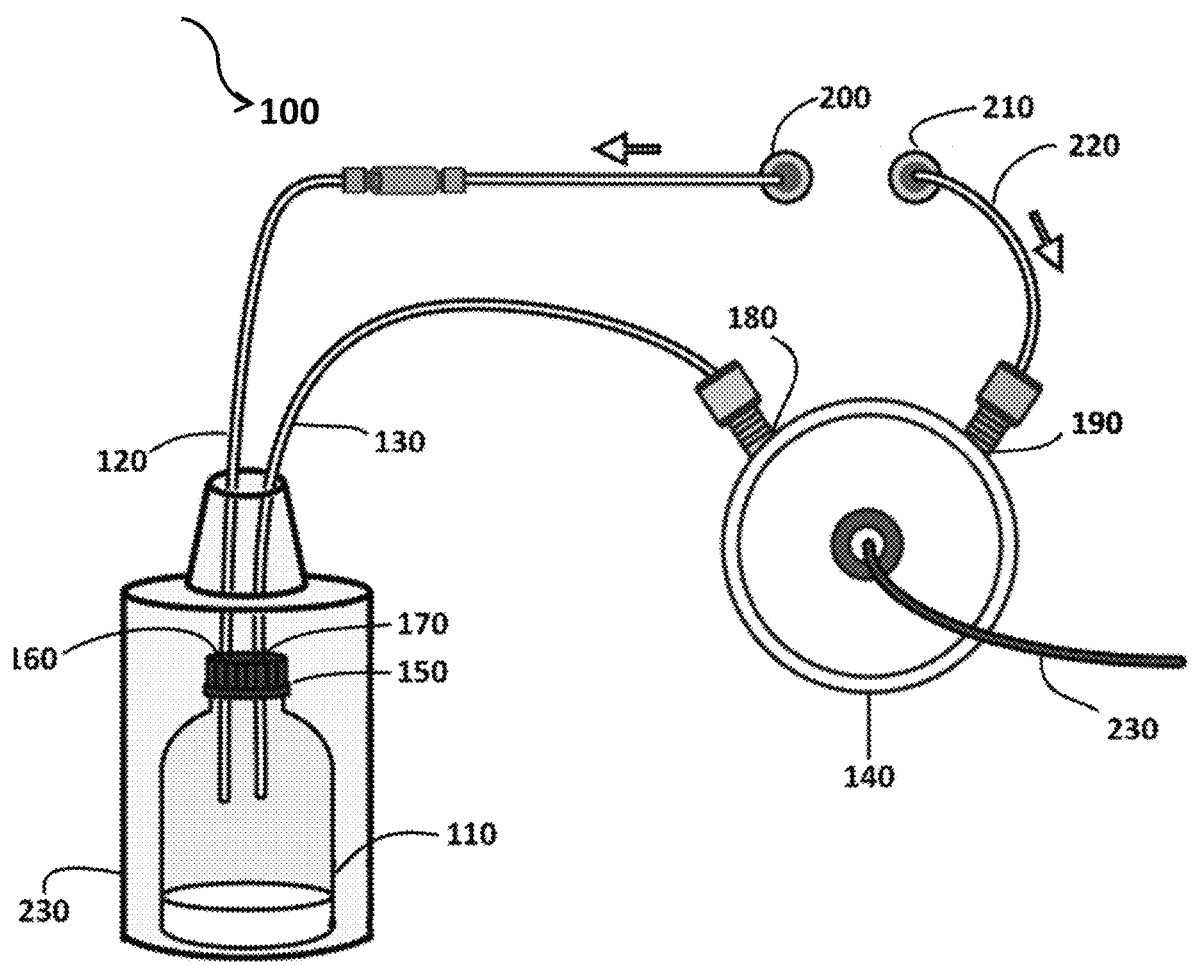
FIG. 2 shows a representation of an electrospray ionization source, which can be used for desolvation gas modification on a mass spectrometer according to one exemplary embodiment.

In some exemplary embodiments, this disclosure provides an electrospray ionization source 100, comprising (i) a container 110, (ii) a sheath gas inlet line 120, (iii) a modified desolvation gas outlet line 130, and (iv) an electrospray ionization probe 140 (See FIG. 2).

In some exemplary embodiments, the disclosure provides a method of characterizing a protein in a sample, comprising (i) supplying the sample to an inlet of an electrospray ionization source 100, (ii) generating ions of components of the protein in the sample at an outlet of the electrospray ionization source, and (iii) analyzing the ions using a mass spectrometer to identify the components of the protein to characterize the protein.

Non-limiting examples of the liquid chromatography device can include reverse phase liquid chromatography, ion-exchange chromatography, size exclusion chromatography, affinity chromatography, hydrophilic-interaction chromatography, and hydrophobic chromatography.

In some exemplary embodiments, the sheath gas inlet line 120 can be a Teflon tube.

In some exemplary embodiments, the sheath gas inlet line 120 can be flexible stainless steel tubing.

In some exemplary embodiments, the sheath gas inlet line 120 can be a tube made using poly ether ether ketone.

In some exemplary embodiments, the modified desolvation gas outlet line 130 can be a Teflon tube.

In some exemplary embodiments, the modified desolvation gas outlet line 130 can be flexible stainless steel tubing.

In some exemplary embodiments, the modified desolvation gas outlet line 130 can be a tube made using poly ether ether ketone.

In some exemplary embodiments, the container 110 can comprise a cap 150. The cap can be safe to sue with mobile phase.

In some exemplary embodiments, the container 110 can comprise a cap 150, wherein the cap can be capable of forming an air-tight seal between the cap and the container. Non-limiting example of caps that can be used include Analytical Sales' Canary-Safe Cap, Restek's Eco-cap bottle top, Restek's Opti-cap bottle top, and VWR's inert mobile phase bottle cap.

In some exemplary embodiments, the cap 150 can comprise of a screw cap.

In some exemplary embodiments, the cap 150 can be made of Polytetrafluoroethylene (PTFE) material.

In some exemplary embodiments, the cap 150 can further comprise of an O-ring to ensure air-tight seal between cap and the container 110.

In some exemplary embodiments, the cap 150 in the container 110 can have at least one port for tubing. In one aspect, the cap 150 in the container 110 can have two ports for tubing.

In some exemplary embodiments, the cap 150 in the container 110 can have at least one inlet port 160.

In some exemplary embodiments, the cap 150 in the container 110 can have at least one outlet port 170.

In some exemplary embodiments, the electrospray ionization probe 140 of the electrospray ionization source 100 can comprise a sheath gas inlet 180.

In some exemplary embodiments, the electrospray ionization source 100 can comprise a container 110 having a cap 150 with an inlet line port 160 and an outlet line port 170 and a sheath gas inlet line 120 capable of providing sheath gas to the inlet line port 160.

In some exemplary embodiments, the electrospray ionization source 100 can comprise a container 110 having a cap 150 with an inlet line port 160 and an outlet line port 170 and a modified desolvation gas outlet line 130 capable of connecting the outlet line port 170 to a sheath gas inlet 180 of an electrospray ionization probe 140.

In some exemplary embodiments, the electrospray ionization probe 140 can be capable of being run in a positive polarity mode.

In some exemplary embodiments, the electrospray ionization probe 140 can be capable of being run in a negative polarity mode.

In some exemplary embodiments, the electrospray ionization probe 140 with an auxiliary gas inlet 190.

In some exemplary embodiments, the electrospray ionization probe 140 can further comprise an electrospray emitter needle.

In some exemplary embodiments, a sheath gas can be provided by a sheath gas source 200 to a container 110 having a cap 150 with an inlet line port 160 through a sheath gas inlet line 120. Non-limiting examples of sheath gas include air, nitrogen.

In some exemplary embodiments, an auxiliary gas can be provided by an auxiliary gas source 210 to an auxiliary gas inlet 190 of an electrospray ionization probe 140 through an auxiliary gas inlet line 220. Non-limiting examples of auxiliary gas include air, nitrogen.

In some exemplary embodiments, the sheath gas that can be provided by a sheath gas source 200 to a container 110 having a cap 150 with an inlet line port 160 through a sheath gas inlet line 120 can be nitrogen gas.

In some exemplary embodiments, the auxiliary gas that can be provided by an auxiliary gas source 210 to an auxiliary gas inlet 190 of an electrospray ionization probe 140 through an auxiliary gas inlet line 220 can be nitrogen gas.

In some exemplary embodiments, the electrospray ionization probe 140 can include an electrospray emitter needle, a sheath gas flow plumbing, and an auxiliary gas flow plumbing.

In some exemplary embodiments, the electrospray ionization source 110 can comprise an electrospray ionization probe 140 which can include an electrospray emitter needle, a sheath gas flow plumbing, and an auxiliary gas flow plumbing, wherein the electrospray ionization probe can be configured to direct flow in the sheath gas flow plumbing coaxially to the electrospray emitter needle.

In some exemplary embodiments, the electrospray ionization probe 140 can be configured to direct flow in the auxiliary gas flow plumbing coaxially to the electrospray emitter needle.

In some exemplary embodiments, the electrospray ionization probe 140 can be a heated electrospray ionization probe.

In some exemplary embodiments, the electrospray ionization probe 140 can be automated to carry out sample aspiration, sample dispensing, sample delivery and/or for spraying the sample.

In some exemplary embodiments, the container 110 having a cap 150 with an inlet line port 160 and a sheath gas inlet line 120, wherein the sheath gas inlet line 120 can be partially inserted into to the inlet line port 160.

In some exemplary embodiments, the cap 150 with an outlet line port 170 and a modified desolvation gas outlet line 130, wherein the modified desolvation gas outlet line 130 can be partially inserted into to the outlet line port 170.

In some exemplary embodiments, the electrospray ionization source 100 can be configured to allow a flow of a sheath gas from the sheath gas inlet line 120 through the container 100 into the desolvation gas outlet line 130.

In some exemplary embodiments, the container 100 can be surrounded by a second container 230. In some specific exemplary embodiments, the second container 230 can be made from polyethylene. In one aspect, the second container 230 can be capable of providing shatter resistant protection for glass bottles. In another aspect, the second container 230 can have an opening in the top.

In some exemplary embodiments, the container 110 can be made form a borosilicate glass material.

In some exemplary embodiments, a volume of the container 110 can range from about 10 ml to about 5000 ml. In one aspect, a volume of the container 110 can be about 10 ml, about 20 ml, about 30 ml, about 40 ml, about 50 ml, about 60 ml, about 70 ml, about 80 ml, about 90 ml, about 100 ml, about 110 ml, about 120 ml, about 130 ml, about 140 ml, about 150 ml, about 160 ml, about 170 ml, about 180 ml, about 190 ml, about 200 ml, about 210 ml, about 220 ml, about 230 ml, about 240 ml, about 250 ml, about 260 ml, about 270 ml, about 280 ml, about 290 ml, about 300 ml, about 310 ml, about 320 ml, about 330 ml, about 340 ml, about 350 ml, about 360 ml, about 370 ml, about 380 ml, about 390 ml, about 400 ml, about 410 ml, about 420 ml, about 430 ml, about 440 ml, about 450 ml, about 460 ml, about 470 ml, about 480 ml, about 490 ml, about 1000 ml, about 1100 ml, about 1200 ml, about 1300 ml, about 1400 ml, about 1500 ml, about 1600 ml, about 1700 ml, about 1800 ml, about 1900 ml, about 2000 ml, about 2500 ml, about 3000 ml, about 3500 ml, about 4000 ml, about 4500 ml, or about 5000 ml.

In some exemplary embodiments, the container 110 can be a pressure resistant container.

In some exemplary embodiments, the container 110 can have a pressure resistance of at least about 0.5 bar gauge. In one aspect, the container 110 can have a pressure resistance of at least about 0.5 bar gauge, at least about 0.6 bar gauge, at least about 0.7 bar gauge, at least about 0.8 bar gauge, at least about 0.9 bar gauge, at least about 1 bar gauge, at least about 1.1 bar gauge, at least about 1.2 bar gauge, at least about 1.3 bar gauge, at least about 1.4 bar gauge, at least about 1.5 bar gauge, at least about 1.6 bar gauge, at least about 1.7 bar gauge, at least about 1.8 bar gauge, at least about 1.9 bar gauge, or at least about 2.0 bar gauge.

In some exemplary embodiments, the container 110 can be capable of being filled with at least one organic solvent. Non-limiting examples of organic solvents include acetonitrile, propanol, isopropanol, water and methanol.

In some exemplary embodiments, the container 110 can be capable of being filled with at least one acid. Non-limiting examples of acid include acetic acid, propionic acid, and formic acid.

In some exemplary embodiments, the container capable 110 of being filled with at least one base. Non-limiting examples of base include ammonia, diethylamine, triethylamine, N,N-diisopropylehtylamine (DIPEA), and piperidine. In some exemplary embodiments, the container capable 110 of being filled with at least one organic solvent and at least one acid.

In some exemplary embodiments, the container capable 110 of being filled with at least one organic solvent and at least one base.

In some exemplary embodiments, the electrospray ionization source 100 can be configured to allow a flow of a sheath gas from the sheath gas inlet line 120 through the container 110 capable of being filled with an organic solvent and an additional chemical component into the desolvation gas outlet line 130.

In some exemplary embodiments, the electrospray ionization source 100 can be capable of providing an electrospray with a solvent flow rate of greater than about 5 µL/min. In one aspect, the electrospray ionization source 100 can be capable of providing an electrospray with a solvent flow rate of greater than about 5 µL/min, greater than about 6 µL/min, greater than about 7 µL/min, greater than about 8 µL/min, greater than about 9 µL/min, greater than about 10 µL/min, greater than about 11 µL/min, greater than about 12 µL/min, greater than about 13 µL/min, greater than about 14 µL/min, greater than about 15 µL/min, greater than about 16 µL/min, greater than about 17 µL/min, greater than about 18 µL/min, greater than about 19 µL/min, greater than about 20 µL/min, greater than about 25 µL/min, greater than about 30 µL/min, greater than about 35 µL/min, greater than about 40 µL/min, greater than about 45 µL/min, greater than about 50 µL/min, greater than about 55 µL/min, greater than about 60 µL/min, greater than about 65 µL/min, greater than about 70 µL/min, greater than about 75 µL/min, greater than about 80 µL/min, greater than about 85 µL/min, greater than about 90 µL/min, greater than about 95 µL/min, greater than about 100 µL/min, greater than about 110 µL/min, greater than about 120 µL/min, greater than about 130 µL/min, greater than about 140 µL/min, greater than about 150 µL/min, greater than about 160 µL/min, greater than about 170 µL/min, greater than about 180 µL/min, greater than about 190 µL/min, greater than about 200 µL/min, greater than about 225 µL/min, greater than about 250 µL/min, greater than about 275 µL/min, greater than about 300 µL/min, greater than about 325 µL/min, greater than about 350 µL/min, greater than about 375 µL/min, greater than about 700 µL/min, greater than about 425 µL/min, greater than about 450 µL/min, or greater than about 500 µL/min.

In some exemplary embodiments, the mass spectrometer 30 can be capable of identifying components of the protein to characterize the protein.

In some exemplary embodiments, the mass spectrometer 30 can be a tandem mass spectrometer.

In some exemplary embodiments, the mass spectrometer 30 can be a tandem in time mass spectrometer.

In some exemplary embodiments, the mass spectrometer 30 can be a tandem in space mass spectrometer.

In some exemplary embodiments, the mass spectrometer 30 can be a hybrid wherein tandem-in-time analyzer can be coupled in space or with tandem-in-space analyzer.

In some exemplary embodiments, the mass spectrometer 30 can be a quadrupole—Orbitrap hybrid mass spectrometer. The quadrupole-Orbitrap hybrid mass spectrometer can be Q Exactive™ Focus Hybrid Quadrupole-Orbitrap™ Mass Spectrometer, Q Exactive™ Plus Hybrid Quadrupole-Orbitrap™ Mass Spectrometer, Q Exactive™ BioPharma Platform, Q Exactive™ UHMR Hybrid Quadrupole-Orbitrap™ Mass Spectrometer, Q Exactive™ HF Hybrid Quadrupole-Orbitrap™ Mass Spectrometer, Q Exactive™ HF-X Hybrid Quadrupole-Orbitrap™ Mass Spectrometer, and Q Exactive™ Hybrid Quadrupole-Orbitrap™ Mass Spectrometer.

In some exemplary embodiments, the mass spectrometer 30 can be a QIT-FTICR.

In some exemplary embodiments, the mass spectrometer 30 can be a Qq-FTICR.

In some exemplary embodiments, the method of characterizing a protein in a sample can comprise detecting or quantifying the protein in the sample.

In one exemplary embodiment, the protein can include an antibody, bispecific antibody, antibody fragment or a multispecific antibody.

In some exemplary embodiments, the protein can be a therapeutic antibody.

In some exemplary embodiments, the protein can be an immunoglobulin protein.

In one exemplary embodiment, immunoglobulin protein can be IgG1.

In one exemplary embodiment, immunoglobulin protein can be IgG4.

In some exemplary embodiments, the protein can be a bispecific antibody.

In some exemplary embodiments, the protein can be an antibody fragment formed on digestion of the antibody.

In one exemplary embodiment, the protein can be a protein variant.

In one exemplary embodiment, the protein can be a post-translationally modified protein.

In one exemplary embodiment, the post-translationally modified protein can be a formed by cleavage, N-terminal extensions, protein degradation, acylation of the N-terminus, biotinylation, amidation of the C-terminal, oxidation, glycosylation, iodination, covalent attachment of prosthetic groups, acetylation, alkylation, methylation, adenylation, ADP-ribosylation, covalent cross links within, or between, polypeptide chains, sulfonation, prenylation, Vitamin C dependent modifications, Vitamin K dependent modification, glutamylation, glycylation, glycosylation, deglycosylation, isoprenylation, lipoylation, phosphopantetheinylation, phosphorylation, sulfation, citrullination, deamidation, formation of disulfide bridges, proteolytic cleavage, ISGylation, SUMOylation or ubiquitination (covalent linkage to the protein ubiquitin).

In one exemplary embodiment, the post-translationally modified protein can be formed on oxidation of a protein.

In another exemplary embodiment, the degradation product can include a post-translation modification of a therapeutic protein.

In another exemplary embodiment, the protein can be a degradation product of a protein.

In yet another exemplary embodiment, the protein can be an impurity found in a biopharmaceutical product.

In another exemplary embodiment, the protein can be an impurity found during the manufacture of the biopharmaceutical product.

In some exemplary embodiments, the protein can be a protein with a pI in the range of about 4.5 to about 9.0. In one aspect, the protein can be a protein with a pI of about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In some exemplary embodiments, the protein can be a product-related impurity. The product related impurity can be molecular variants, precursors, degradation products, fragmented protein, digested product, aggregates, post-translational modification form or combinations thereof.

In some specific exemplary embodiments, the protein can be a process-related impurity. The process-related impurity can include impurities derived from the manufacturing process, e.g., nucleic acids and host cell proteins, antibiotics, serum, other media components, enzymes, chemical and biochemical processing reagents, inorganic salts, solvents, carriers, ligands, and other leachables used in the manufacturing process.

In some specific exemplary embodiments, the protein can be an impurity. In one exemplary embodiment, the number of impurities in the sample can be at least two.

In some exemplary embodiments, the mobile phase used to elute the protein can be a mobile phase that can be compatible with a mass spectrometer.

In some exemplary embodiments, the mobile phase used in the liquid chromatography device can include water, acetonitrile, trifluoroacetic acid, formic acid, or combination thereof.

In some exemplary embodiments, the mobile phase can have a flow rate of about 0.1 ml/min to about 0.4 ml/min in the liquid chromatography device. In one aspect, the flow rate of the mobile phase in the liquid chromatography device can be about 0.1 ml/min, about 0.15 ml/min, about 0.20 ml/min, about 0.25 ml/min, about 0.30 ml/min, about 0.35 ml/min, or about 0.4 ml/min.

It is understood that the system is not limited to any of the aforesaid protein, impurity, mobile phase, mass spectrometer, organic solvent, acid, base, or chromatographic column.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is incorporated by reference, in its entirety and for all purposes, herein.

The disclosure will be more fully understood by reference to the following Examples, which are provided to describe the disclosure in greater detail. They are intended to illustrate and should not be construed as limiting the scope of the disclosure.

Examples

Materials. Deionized water was provided by a Milli-Q integral water purification system installed with a MilliPak Express 20 filter (Millipore Sigma, Burlinton, Mass.). NIST Monoclonal Antibody Reference Material 8671 (NISTmAb, humanized IgG1K monoclonal antibody) was purchased from National Institute of Standards and Technology (Gaithersburg, Md.). Rapid Peptide N-glycosidase F (Rapid PNGase F) with 5× Rapid PNGase F buffer was purchased from New England Biolabs Inc. (Ipswich, Mass.). TCEP-HCl (tris(2-carboxyethyl) phosphine hydrochloride), Tris-HCl pH 7.5 (UltraPure), trifluoroacetic acid (LC-MS grade), formic acid (LC-MS grade), and acetonitrile (Optima LC/MS grade) were purchased from Thermo Fisher Scientific (Waltham, Mass.), trypsin (sequencing grade) was purchased from Promega (Madison, Mich.). Iodoacetamide, propionic acid and acetic acid were purchased from Sigma Aldrich, Co. (St. Louis, Mo.). 2-propanol (HPLC grade) was purchased from VWR International, LLC (Radnor, Pa.).

Safety Considerations. For desolvation gas modified experiments, the sheath gas was set to 15 arbitrary units. A higher setting might be possible, but the pressure within the bottle should be measured and made sure not to exceed the pressure rating of the bottle. A pressure resistant bottle (e.g., Duran pressure plus bottle, pressure rating: +1.5 bar) was high recommended for this application. A secondary container was also required for this setup to prevent possible acid or base spills.

Example 1

1.1 Sample Preparation.

NISTmAb stock sample (100 μg) was diluted into 5 mM acetic acid and reduced with 5 mM TCEP-HCl at 80° C. for 10 min. After adjusting the pH to 7.5 using 1 M Tris-HCl (pH 7.5), 10 mM iodoacetamide and 5 μg of trypsin (E/S ratio at 1:20) were added, and the sample was incubated at 37° C. for 3 hours. Finally, the solution was acidified by 1% TFA to quench the digestion.

1.2 LC-MS Analysis.

For peptide mapping analysis of NISTmAb, aliquots (2 μg) of digests were separated using an ACQUITY UPLC Peptide BEH C18 Column (130 Å, 1.7 μm, 2.1 mm×150 mm) (Waters, Milford, Mass.) for online LC-MS/MS analysis on a Q-Exactive mass spectrometer. For the separation, the mobile phase A was 0.1% FA (v/v) in water, and mobile phase B was 0.1% FA in acetonitrile (ACN). Detailed LC gradient and MS parameters are included in the Tables 1 and 2 respectively.

TABLE 1

LC gradient for peptide mapping analysis

| Mobile Phase | A: 0.05% Trifluoroacetic Acid in Water or 0.1% Formic Acid in Water |
| --- | --- |
| | B: 0.045% Trifluoroacetic Acid in Acetonitrile or 0.1% Formic Acid in Acetonitrile |
| Column | Waters ACQUITY UPLC Peptide BEH C18 130 Å, 1.7 μm, 2.1 mm × 150 mm column |
| Column Temperature | 40° C. |

| Gradient | Time (min) | Flow (μL/min) | % A | % B |
| --- | --- | --- | --- | --- |
| | 0.0 | 0.250 | 99.9 | 0.1 |
| | 5.0 | 0.250 | 99.9 | 0.1 |
| | 80.00 | 0.250 | 65.0 | 35.0 |
| | 80.10 | 0.250 | 10.0 | 90.0 |
| | 90.00 | 0.250 | 10.0 | 90.0 |
| | 91.00 | 0.250 | 99.9 | 0.1 |
| | 105.00 | 0.250 | 99.9 | 0.1 |

TABLE 2

MS parameters for peptide mapping analysis

| MS parameters | Control Experiment | Desolvation gas modified method (w/PA/IPA) |
| --- | --- | --- |
| Probe heater temperature [° C.] | 250 | 250 |
| Source voltage [kV] | 3.8 | 3.8 |
| Capillary temperature [° C.] | 320 | 320 |
| S-lens RF level | 60 | 60 |
| Sheath gas | 40 | 15[a] |
| Aux gas | 10 | 10 |
| Sweep gas | 0 | 0 |
| Scan range [m/z] | 300-2000 | 300-2000 |

[a] the sheath gas setting was reduced to 15 arbitrary units to reduce the pressure within the solvent bottle.

1.3 Results

Figure 3:
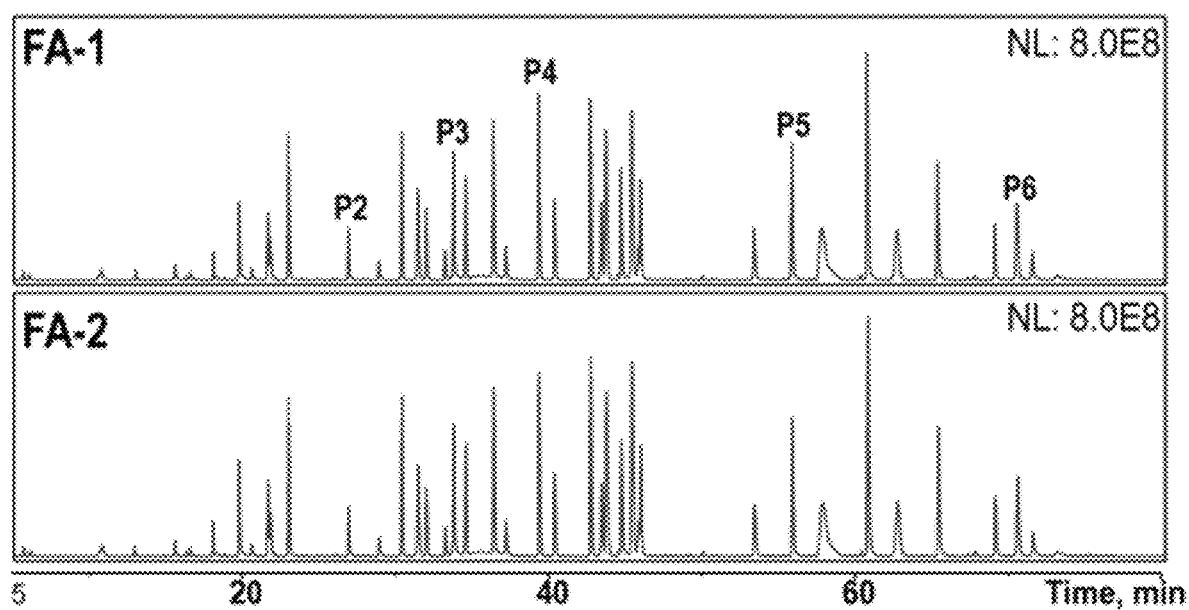
FIG. 3 shows base peak chromatograms from the LC-MS analysis of NISTmAb digests using formic acid (FA)-based method according to one exemplary embodiment.

FIG. 3 shows the base peak chromatograms (BPCs) from the LC-MS analysis of the tryptic digests of NISTmAb using FA as a mobile phase with a BEH C18 column.

Example 2

2.1 Sample Preparation.

Sample preparation was carried out as described in 1.1

2.2 LC-MS Analysis.

For peptide mapping analysis of NISTmAb, aliquots (2 μg) of digests were separated using an ACQUITY UPLC Peptide BEH C18 Column (130 Å, 1.7 μm, 2.1 mm×150 mm) (Waters, Milford, Mass.) for online LC-MS/MS analysis on a Q-Exactive mass spectrometer. For the separation, mobile phase A was 0.05% TFA (v/v) in water, and mobile phase B was 0.045% TFA (v/v) in ACN. The LC gradient and MS parameters implemented are included in the Tables 1 and 2 respectively.

2.3 Results

Figure 4:
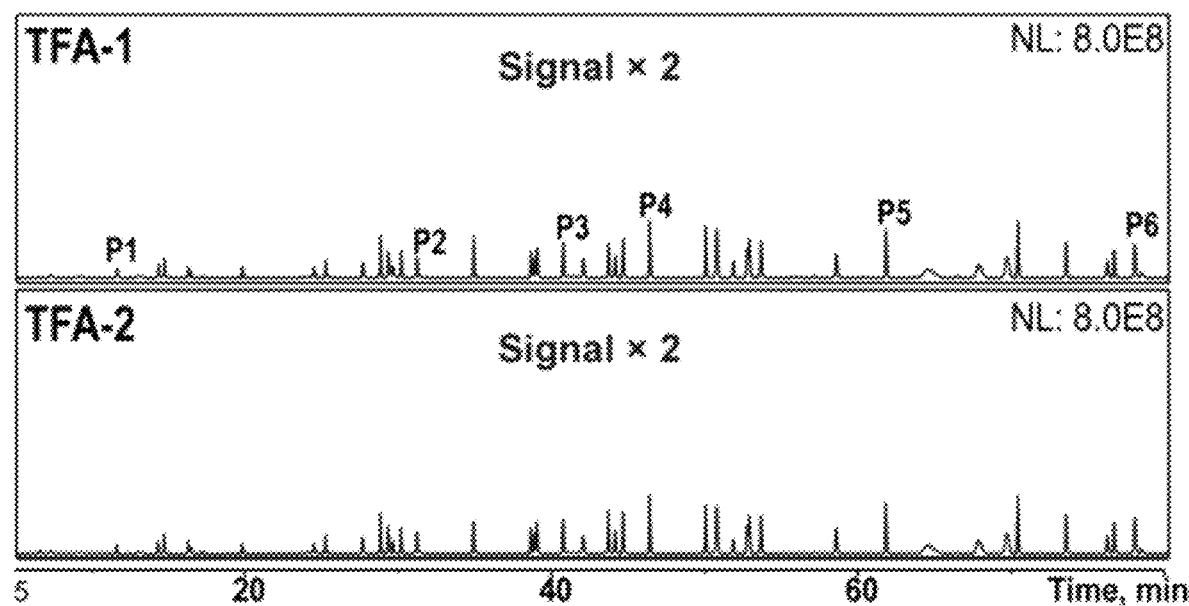
FIG. 4 shows base peak chromatograms from the LC-MS analysis of NISTmAb digests using trifluoroacetic acid-based method according to one exemplary embodiment.

FIG. 4 shows the base peak chromatograms (BPCs) from the LC-MS analysis of the tryptic digests of NISTmAb using TFA as a mobile phase with a BEH C18 column. On comparing the BPCs in FIGS. 3 and 4, it is evident that the separation and retention of tryptic peptides on the C18 column were significantly different using either FA or TFA as mobile phase modifier. In general, TFA outperforms FA from the chromatographic performance perspective, exhibiting better retention of hydrophilic peptides, better peak shapes and overall higher peak capacity. For example, a small tryptic peptide EYK (P1, FIG. 4) was not retained on the C18 column when FA was used, whereas it is retained on the same column when TFA was applied. This feature might improve the sequence coverage of protein biopharmaceuticals from the peptide mapping analysis. On the other hand, TFA-based analysis exhibited a significant loss in MS sensitivity comparing to FA-based analysis.

Example 3

3.1 Sample Preparation.

Sample preparation was carried out as described in 1.1

3.2 LC-MS Analysis.

LS-MS analysis was carried out as described in 2.2.

3.3 Modification of the Desolvation Gas

The sheath gas flow from a Q-Exactive mass spectrometer was redirected to a Duran pressure plus bottle (SCHOTT North America, Inc., Elmsford, N.Y.) through a Canary-Safe Cap (Analytical Sales and Services, Inc., Flander, N.J.) using ⅛" TEFLON tubing (FIG. 1). The outgoing tubing from the bottle was then connected back to the HESI-II probe in a Thermo Scientific Ion Max ion source. For peptide mapping analysis, 150 mL of propionic acid (PA) and 50 mL of isopropanol (IPA) were mixed and transferred into the bottle. The bottle containing PA and IPA was then placed into a polyethylene secondary container (BEL-ART acid/solvent bottle carrier, Wayne, N.J.) with a 16 mm opening in the top for insertion of tubing. To disable the modification, the sheath gas tubing was directly connected to the HESI-II probe without passing through the device.

3.4 Results

Figure 5:
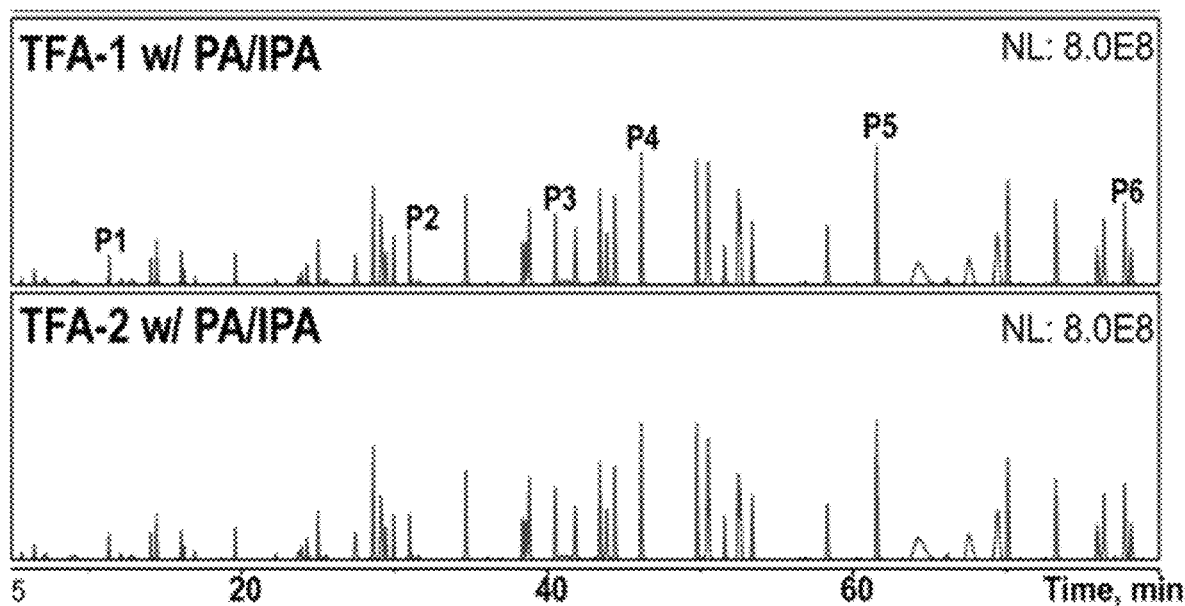
FIG. 5 shows base peak chromatograms from the LC-MS analysis of NISTmAb digests using trifluoroacetic acid (TFA)—based method with PA/IPA modified desolvation gas according to one exemplary embodiment, wherein the MS signal from TFA control experiments have been amplified two times for better visualization

FIG. 5 shows the base peak chromatograms (BPCs) from the LC-MS analysis of the tryptic digests of NISTmAb using trifluoroacetic acid as mobile phase with a BEH C18 column with desolvation modification enabled. On comparing the BPCs in FIG. 5 (TFA-containing mobile phase, desolvation gas modification enabled) with FIG. 3 (FA-containing mobile phase, desolvation gas modification disabled) and FIG. 4 (TFA-containing mobile phase, desolvation gas modification disabled), it is evident that modification of the desolvation gas with acid vapor from PA and IPA led to a significant increase in MS sensitivity for TFA-based analysis.

As demonstrated by six representative tryptic peptides of different size and retention time (Table 3 below), 4.9-5.8 folds of increase in MS sensitivity were readily achieved by this approach, regardless of the peptide size and mobile phase composition. In addition, a subtle increase in charge states were also consistently observed for many tryptic peptides after the desolvation gas modification. This feature might lead to improved spectral quality of tandem MS due to more efficient fragmentation of highly charged species, and subsequently resulting in more confident identification. Overall, by modifying the desolvation gas with acid vapor using the developed device, a significantly more sensitive peptide mapping method can be readily achieved. The gained MS sensitivity is of great value to characterize low-abundance attributes present in protein biopharmaceuticals, such as PTMs and sequence variants.

TABLE 3

Comparison of the MS intensities and averaged charge
states of six representative tryptic peptides
from NISTmAb analyzed under the three conditions.

| Tryptic peptides | MS intensities (ion counts)/ averaged charge states | | | Increase (folds) |
|---|---|---|---|---|
| | FA | TFA control | TFA w/ PA/IPA | |
| P1: EYK | NA | 9.7E+07/ z = 1.00 | 4.3E+08/ z = 1.00 | NA |
| P2: VDNALQSGNSQESVTE QDSK | 3.4E+09/ z = 2.65 | 4.9E+08/ z = 2.19 | 2.4E+09/ z = 2.19 | 4.9 |
| P3: VYACEVTHQGLSSPVTK | 8.5E+09/ z = 2.81 | 1.05E+09/ z = 2.21 | 6.0E+09/ z = 2.57 | 5.7 |
| P4: STSGGTAALGCLVK | 8.3E+09/ z = 1.96 | 1.2E+09/ z = 1.88 | 5.6E+09/ z = 1.89 | 4.9 |
| P5: TTPPVLDSDGSFFLYSK | 9.4E+09/ z = 2.16 | 1.3E+09/ z = 1.98 | 7.7E+09/ z = 2.00 | 5.8 |
| P6: DYFPEPVTVSWNSGAL TSGVHTFPAVLQSSGLYS LSSVVTVPSSSLGTQT YICNVNHKPSNTK | 4.5E+09/ z = 5.47 | 7.1E+08/ z = 4.81 | 4.0E+09/ z = 5.05 | 5.7 |

Example 4

4.1 Sample Preparation.

Initial sample preparation was carried out as described in 1.1. However, to evaluate if the new approach can be applied to continuous analysis and if the improved sensitivity can be maintained over a long period of time for peptide mapping analysis, NISTmAb digests were repeatedly performed over two consecutive days.

4.2 LC-MS Analysis.

LS-MS analysis was carried out as described in 2.2.

4.3 Modification of the Desolvation Gas

The desolvation gas modification was carried out as described in 3.3.

4.4 Results

Figure 6:
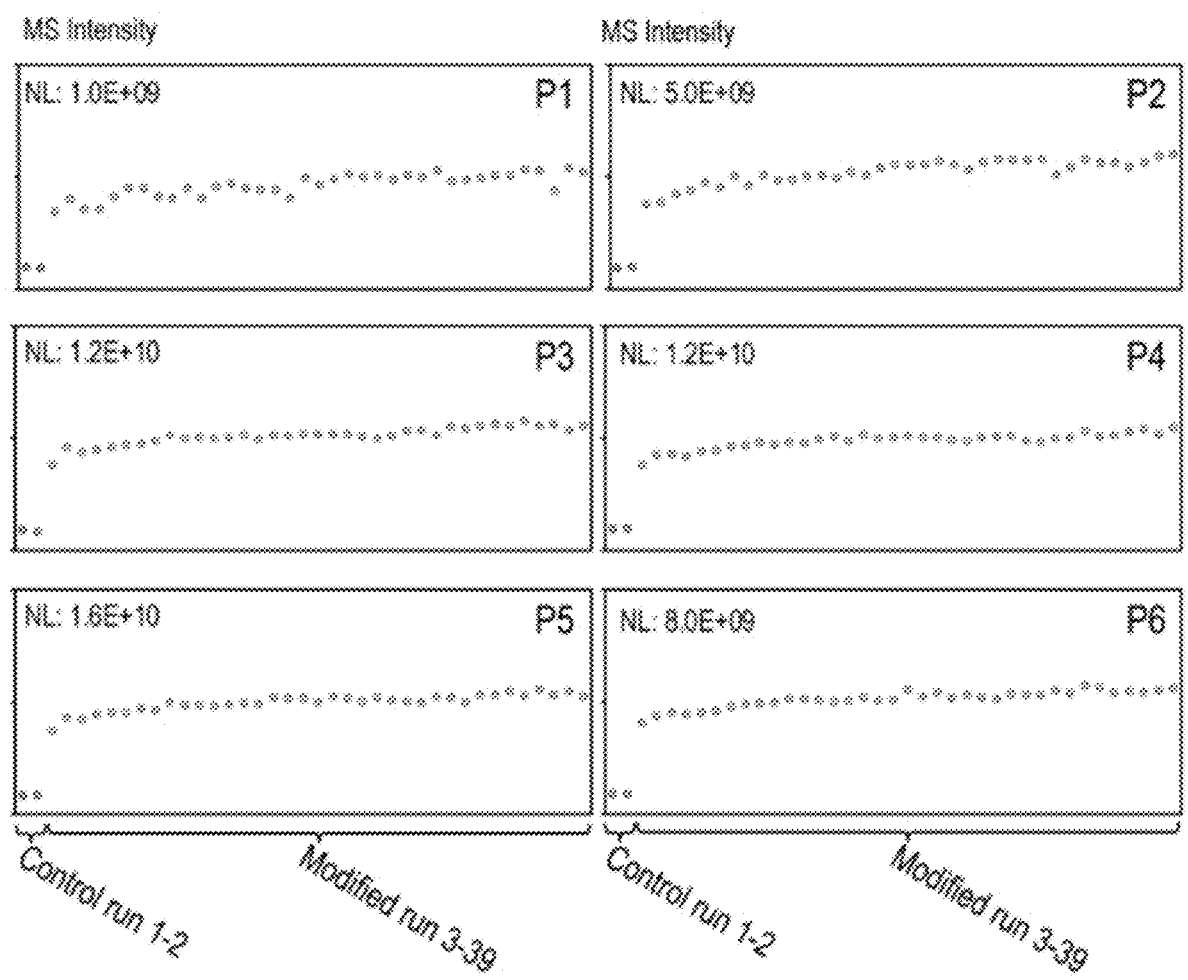
FIG. 6 shows MS intensities of six representative tryptic peptides from NISTmAb digests using control method (run 1-2) and desolvation gas modified method (run 3-39) wherein the desolvation gas modified method is performed according to one exemplary embodiment.

Again, after enabling the desolvation gas modification with acid vapor as described in 3.3, the increase in MS sensitivity, comparing to the control method (as described in example 3), was immediately achieved and maintained for at least 37 consecutive runs (~3800 min) as tested (See FIG. 6). The consumption of the PA and IPA mixture, under the applied experimental conditions, was estimated to be 1 mL per hour. As a result, the developed approach is highly suitable for routine peptide mapping analysis of protein biopharmaceuticals, where continuous analysis of large sample sets might be frequently required.

Example 5

Examples 1-4 illustrate the results of using the desolvate gas approach for peptide mapping analysis. To evaluate if the same approach can be utilized to improve the intact mass analysis for protein biopharmaceuticals via charge reduction, an experiment using the desolvation gas approach with weak base was conducted.

5.1 Sample Preparation 10 mM TCEP-HCl was added to diluted NISTmAb solution (1 μg/μL), and the sample was incubated at 50° C. for 30 minutes. To remove the N-glycans present on reagent protein X, the protein sample was first diluted to 0.25 μg/μL using 5× Rapid PNGase F buffer (containing reducing agent), and the solution was then incubated at 80° C. for 10 min. Subsequently, Rapid PNGase F was added to the solution, and the sample was incubated at 50° C. for 30 minutes.

5.2 RPLC Analysis

For intact mass analysis of reduced NISTmAb and reagent protein X. Aliquots (4 μg) of each sample were separated using a BioResolve RP mAb Polyphenyl column (50 mm×2.1 mm, 2.7 μm) (Waters, Milford, Mass.) for online LC-MS analysis on a Q-Exactive mass spectrometer. The detailed LC gradient and MS parameters are included in the Tables 4 and 5, respectively.

TABLE 4

LC gradient for intact mapping analysis

| Mobile Phase | A: 0.1% Formic Acid in Water |
| | B: 0.1% Formic Acid in Acetonitrile |
| Column | Waters BioResolve RP mAb Polyphenyl, 450 Å, 2.7 μm, 2.1 × 50 mm column |
| Column Temperature | 80° C. |

| Gradient | Time (min) | Flow (μL/min) | % A | % B |
|---|---|---|---|---|
| | 0.0 | 0.250 | 85.0 | 15.0 |
| | 10.0 | 0.250 | 45.0 | 55.0 |
| | 10.15 | 0.250 | 20.0 | 80.0 |
| | 10.65 | 0.250 | 20.0 | 80.0 |
| | 10.80 | 0.250 | 85.0 | 15.0 |
| | 12.50 | 0.250 | 85.0 | 15.0 |

TABLE 5

MS parameters for intact mass analysis of
reduced NISTmAb and reagent protein X

| MS parameters | Control Experiment | Desolvation gas modified method w/1% TEA in ACN |
|---|---|---|
| Probe heater temperature [° C.] | 250 | 250 |
| Source voltage [kV] | 3.5 | 3.5 |
| Capillary temperature [° C.] | 350 | 350 |
| S-lens RF level | 60 | 60 |
| Sheath gas | 20 | 15[a] |
| Aux gas | 10 | 10 |
| Sweep gas | 0 | 0 |
| Scan range [m/z] | 800-4000 | 1500-5500[b] |
| SID [eV] | 0 | 75 |

[a] the sheath gas setting was reduced to 15 arbitrary units to reduce the pressure within the solvent bottle.
[b] the scan region was changed due to the charge reduction.

5.3 Modification of the Desolvation Gas

The sheath gas flow from a Q-Exactive mass spectrometer was redirected to a Duran pressure plus bottle (SCHOTT North America, Inc., Elmsford, N.Y.) through a Canary-Safe Cap (Analytical Sales and Services, Inc., Flander, N.J.) using ⅛" TEFLON tubing (See FIG. 1). The outgoing tubing from the bottle was then connected back to the HESI-II probe in a Thermo Scientific Ion Max ion source. For intact mass analysis, 1% triethylamine (TEA) (v/v) in 200 mL of acetonitrile was transferred into the bottle. The bottle containing concentrated acid or base was then placed into a polyethylene secondary container (BEL-ART acid/solvent bottle carrier, Wayne, N.J.) with a 16 mm opening in the top for insertion of tubing. To disable the modification, the sheath gas tubing was directly connected to the HESI-II probe without passing through the device.

5.4 Results

Figure 7:
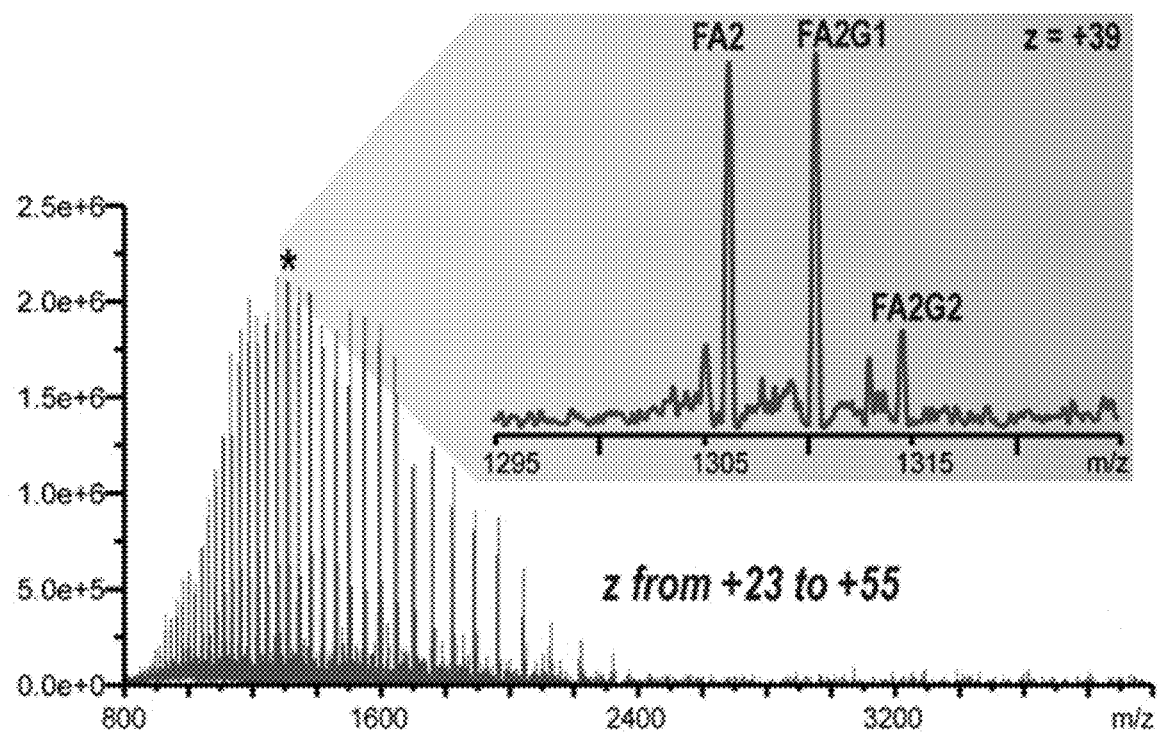
FIG. 7 shows the mass spectra of reduced heavy chain of NISTmAb using the control method carried out according to one exemplary embodiment.
Figure 8:
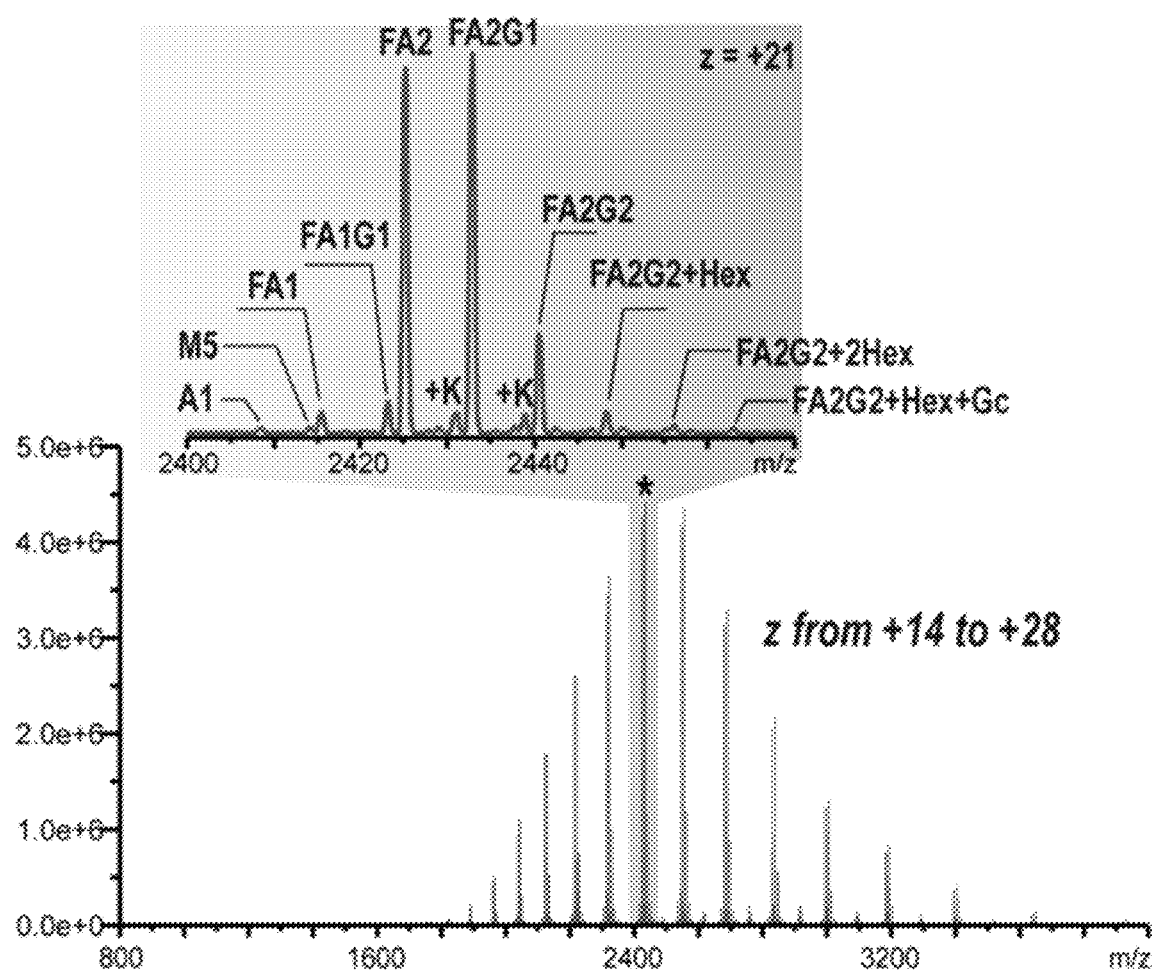
FIG. 8 shows the mass spectra of reduced heavy chain of NISTmAb using the charge reduction method carried out according to one exemplary embodiment.

To evaluate if similar improvements can be achieved via desolvation gas modification, reduced NISTmAb was used as a testing article. Triethylamine (TEA) was diluted to 1% (v/v) using acetonitrile (ACN) and used to deliver the base vapor into desolvation gas. After chromatographic separation on a reversed-phase (RP) polyphenol column, the MS spectra of reduced heavy chain of NISTmAb acquired from a control method and from the desolvation gas modified method were both shown in FIG. 7 (control method) and FIG. 8 (charge reduction method). After enabling the modification, a significant charge reduction on NISTmAb heavy chain, from charge states +23 to +55 to charge states +14 to +28, was achieved. Close examination of charge state +39 from the control method revealed a high level of background noise, which was likely attributed to the decay of the highly charged heavy chain species during the MS analysis, such as neutral losses from water (−18 Da), ammonia (−17 Da) and carboxylic acid (−44 Da) as well as protein backbone fragmentation.

Figure 9:
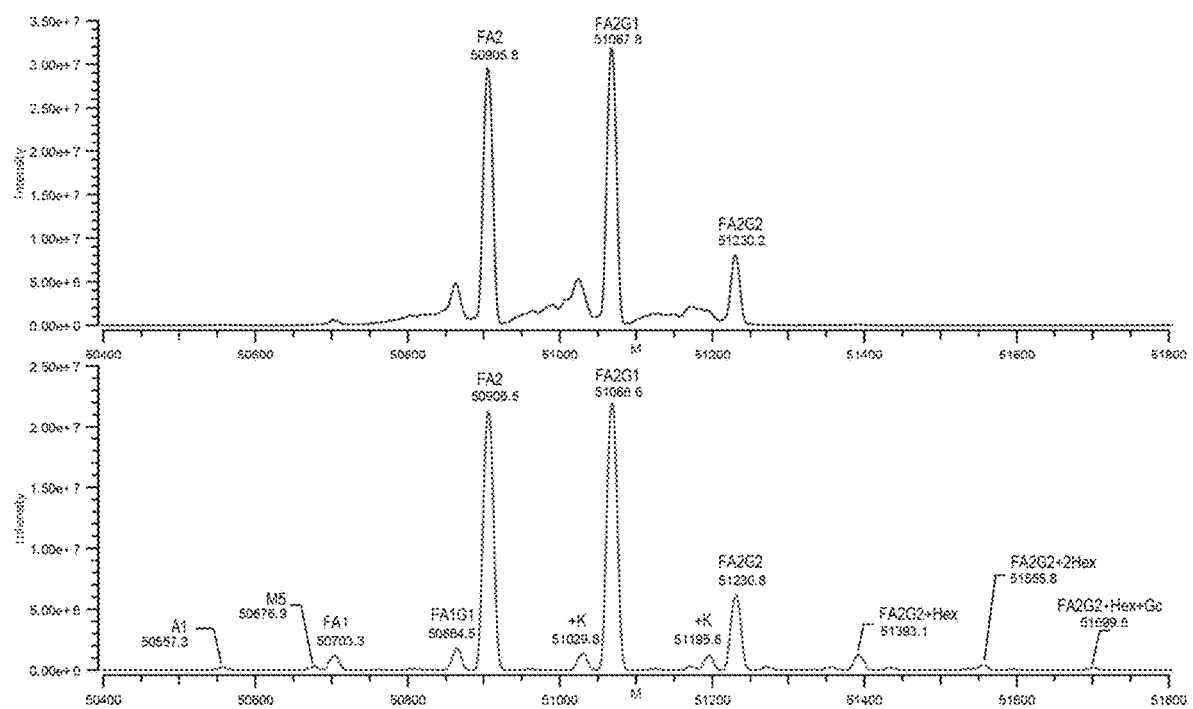
FIG. 9 shows deconvoluted mass spectra of reduced heavy chain of NISTmAb using control method (top panel) and charge reduction method (bottom panel) carried out according to one exemplary embodiment.
Figure 10:
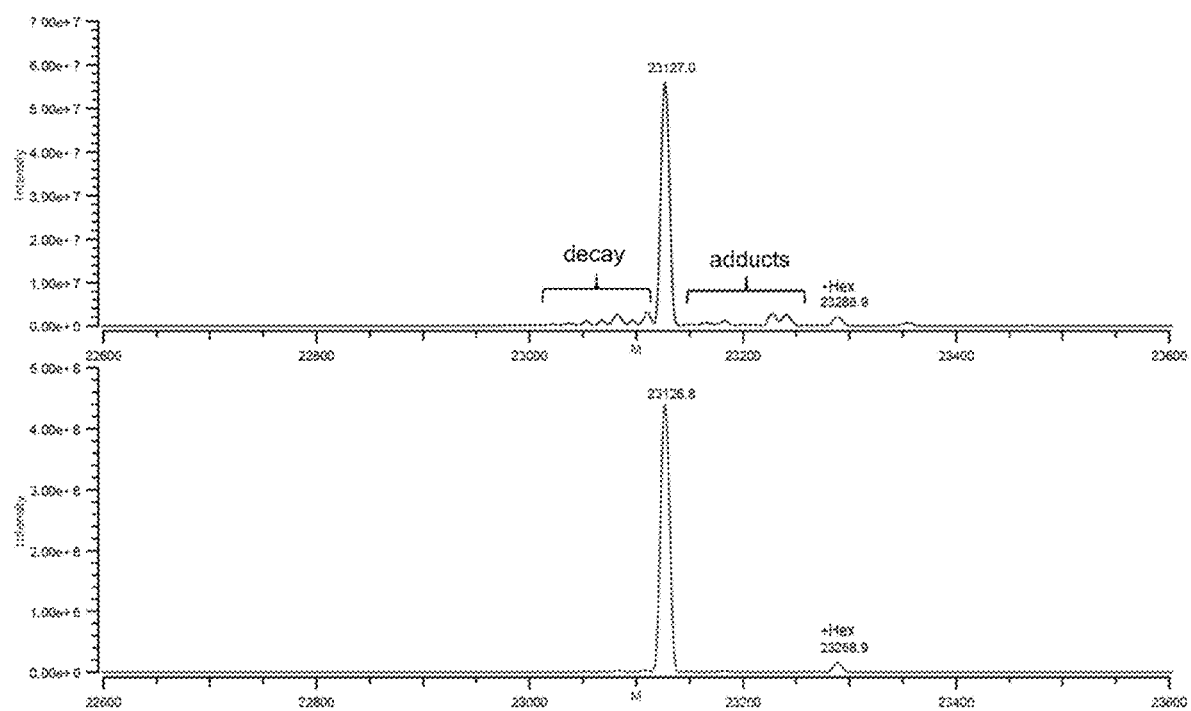
FIG. 10 shows deconvoluted mass spectra of reduced light chain of NISTmAb using control method (top panel) and charge reduction method (bottom panel) carried out according to one exemplary embodiment.

On the contrary, the zoom-in view of charge state +21 from the modified method exhibited greatly improved signal to noise ratio, thus allowing the identification of several low abundance glycoforms that are not detected in the control method. The deconvoluted mass spectrum (See FIG. 9) and mass analysis (Table 6) further demonstrated that the improved method could accurately identify glycoforms present at as low as 0.3% on the heavy chain of NISTmAb. The improvement in spectral quality is not only attributed to greatly simplified spectrum due to less crowded charge state envelopes, but more importantly is a result of stabilized protein analytes. This is consistent with the well-established knowledge that the collision energy associated with a protein ion during MS analysis is proportional to its charge state. Specifically, lower charge states decay slower than the higher charge states of the same analyte during the analysis within orbitrap. Notably, efforts to mitigate the extensive decay of highly charged heavy chain species from the control method were not successful, even after completely removing the source-induced dissociation (SID) energy. On the contrary, high levels of SID energy (75 eV used in this experiment) can be readily tolerated from the charge reduction method without noticeable decay or fragmentation of heavy chain, which further improves the spectral quality via more efficient desolvation and adduct removal. Similar improvement in spectral quality was also achieved for the reduced light chain of NISTmAb (See FIG. 10). It is worth noting that application of charge reduction strategy to improve MS spectral quality is most helpful for fully denatured and reduced proteins, as they are often highly charged (due to increased protein surface areas (Kaltashov and Mohimen. Analytical chemistry 2005, 77, 5370-5379)) during ESI-MS analysis and are most susceptible to undesired fragmentation and decay.

TABLE 6

| Glycan | Average Glycan Mass (Da) | % Peak Area | Theoretical Mass of Glycosylated Heavy Chain (Da) | Observed Glycosylated Heavy Chain Mass (Da) |
|---|---|---|---|---|
| A1 | 1096.0 | 0.4% | 50557.5 | 50557.3 |
| M5 | 1217.1 | 0.5% | 50678.6 | 50676.9 |
| FA1 | 1242.1 | 2.1% | 50703.6 | 50703.3 |
| FA1G1 | 1404.3 | 2.9% | 50865.8 | 50864.5 |
| FA2 | 1445.3 | 39.3% | 50906.8 | 50906.5 |
| FA2G1 | 1607.5 | 40.4% | 51069.0 | 51068.6 |
| FA2G2 | 1769.6 | 11.1% | 51231.1 | 51230.8 |
| FA2G2 + Hex | 1931.7 | 2.3% | 51393.2 | 51393.1 |
| FA2G2 + 2Hex | 2093.9 | 0.7% | 51555.4 | 51555.8 |
| FA2G2 + Hex + Gc | 2239.0 | 0.3% | 51700.5 | 51699.8 |

Example 6

In addition, the developed charge reduction method, as achieved by modifying the desolvation gas with TEA, can also be utilized to tackle high mass heterogeneity present in complex protein samples. Those might include various protein reagents that are critically important to support different assays during the development of protein biopharmaceuticals. Using intact mass analysis to confirm the identities of those protein reagents, no matter if they are obtained from commercial sources or produced in-house is frequently required to support the subsequent studies. Some protein reagents are highly heterogeneous in molecular weight due to extensive glycosylation, which can present significant challenges for routine intact mass method. To demonstrate the utility of the developed charge reduction method, a complex reagent protein (Protein X) with high mass heterogeneity was used as a testing article.

6.1 Sample Preparation.

Figure 11:
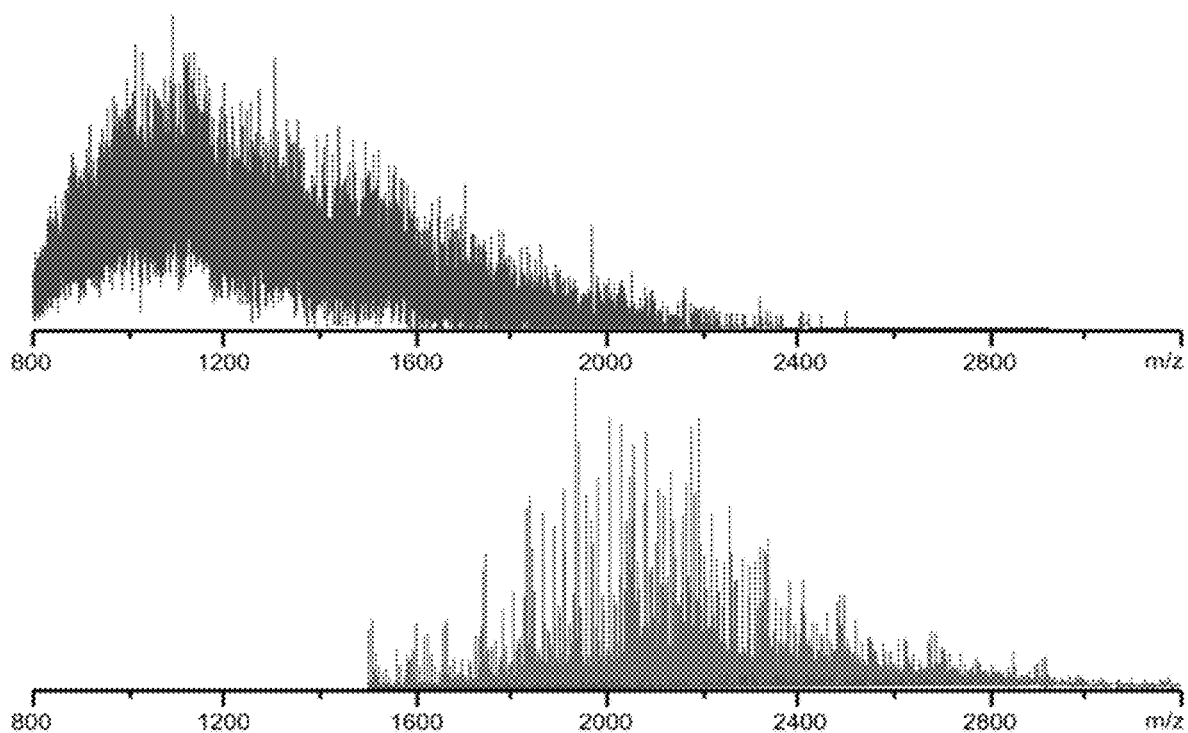
FIG. 11 shows the raw mass spectra of a highly heterogeneous protein with multiple O-glycans using a LC-MS analysis acquired using normal method (top panel) and charge reduction method (bottom panel) according to one exemplary embodiment.

Prior to the analysis, Protein X was first treated with PNGase F under both denaturing and reducing conditions, in order to remove the mass heterogeneity introduced by the presence of N-glycans. As shown in FIG. 11, even after the PNGase F treatment, Protein X exhibited a highly convoluted MS spectrum that cannot be deciphered using a regular intact mass method. This was likely attributed to the overlapping charge envelopes from different co-eluting mass forms of this molecule at low m/z region.

6.3 Modification of the Desolvation Gas.

The desolvation gas modification was carried out as described in 5.3.

6.4 Results

Figure 12:
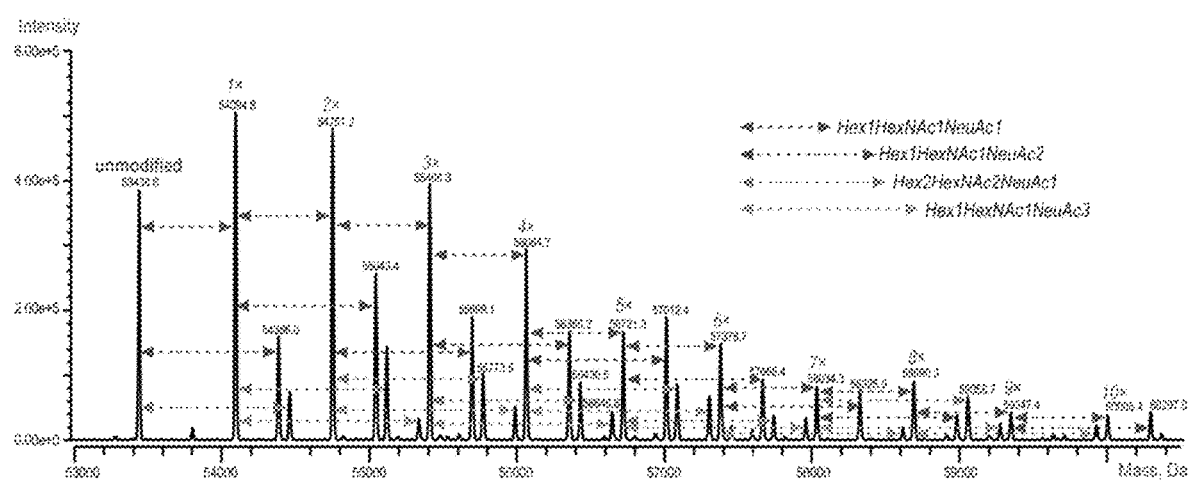
FIG. 12 shows the deconvoluted mass spectrum of a highly heterogeneous protein with multiple O-glycans using a LC-MS analysis acquired using charge reduction method according to one exemplary embodiment.

In contrast to results obtained for example 6.1, after enabling the desolvation gas modification with TEA, the MS signal of the same sample was immediately shifted to high m/z region and exhibiting much better resolved charge states. Subsequently, the deconvoluted spectrum (See FIG. 12) clearly revealed that this protein was extensively modified by O-glycans with possibly 10 different glycosylation sites and four different O-glycan forms. Overall, nearly thirty five different mass species from this protein were confidently identified and assigned. It is worth noting that the dramatically improved spectral quality might also be partly attributed to more stabilized protein ions after charge reduction, as the polysaccharide moiety on this molecule could be labile under regular ESI-MS conditions.

Finally, for some other LC-MS based intact mass methods, where the use of TFA is inevitable to ensure chromatographic performance, the developed approach was also tested to counteract TFA ion suppression at protein level using PA/IPA modified desolvation gas. For example, hyphenation of size exclusion chromatography (SEC) to MS using mobile phases containing acetonitrile, TFA, and formic acid has been used for reduced mAb analysis. (Liu et al. Journal of the American Society for Mass Spectrometry 2009, 20, 2258-2264.) Hyphenation of hydrophilic interaction chromatography to MS using TFA-containing mobile phases has been used to study the low molecular weight impurities in mAb samples (Wang et al. Journal of pharmaceutical and biomedical analysis 2018, 154, 468-475). In both methods, significant improvement in MS sensitivity can be achieved for many mAb fragments (e.g. heavy chain, light chain and smaller fragments) using PA/IPA modified desolvation gas. However, the MS sensitivity of intact mAb (~150 kDa) did not improve as a result of this modification. This finding is also consistent with the previous study (Apffel et al. Journal of chromatography. A 1995, 712, 177-190) which hypothesizes that a larger protein might accommodate a greater number of TFA anions, which cannot be effectively replaced by PA during the ESI process.

Thus, an effective approach to improve the data quality from both peptide mapping analysis and intact mass analysis via desolvation gas modification using a simple device is demonstrated. By using PA/IPA modified desolvation gas, the TFA ion suppression from a typical peptide mapping method can be effectively mitigated, and thus leading to significantly improved MS sensitivity. The developed approach can be easily implemented without changing the LC method and is capable of continuous analysis of large sample sets, making it particularly suitable for routine characterization of protein biopharmaceuticals. By using TEA modified desolvation gas, the new approach could also be utilized to improve the intact mass analysis of proteins via charge reduction. Significant improvement in spectral quality not only allows the detection of minor mass forms otherwise buried in noise, but also enables the mass measurement of highly heterogeneous proteins. Finally, with the ever-increasing role played by LC-MS technique in protein biopharmaceutical characterization, the developed approach can make a deeper and broader contribution by serving as a low-cost and practical solution to improve the analytical capability and better support the drug development.

What is claimed is:

1. An electrospray ionization source, comprising:
   a container having a cap, wherein the cap has an inlet line port and an outlet line port, wherein the container comprises an organic solvent and an acid, wherein a volume of said organic solvent is less than a volume of said acid;
   a sheath gas inlet line for providing a sheath gas to the inlet line port; and
   a modified desolvation gas outlet line capable of connecting the outlet line port to a sheath gas inlet of an electrospray ionization probe.

2. The electrospray ionization source of claim 1, wherein the organic solvent is selected from a group consisting of acetonitrile, propanol, isopropanol, water and methanol.

3. The electrospray ionization source of claim 1, wherein the acid is selected from a group consisting of acetic acid, propionic acid, and formic acid.

4. The electrospray ionization source of claim 1, wherein a ratio of organic solvent to acid in the container is about 1:3.

5. The electrospray ionization source of claim 1, wherein the organic solvent is isopropanol.

6. The electrospray ionization source of claim 1, wherein the acid is propionic acid.

7. The electrospray ionization source of claim 1, wherein the electrospray ionization probe comprises an auxiliary gas inlet.

8. The electrospray ionization source of claim 7, wherein the auxiliary gas inlet is supplied with an auxiliary gas.

9. The electrospray ionization source of claim 1, wherein the electrospray ionization probe comprises an electrospray emitter needle, a sheath gas flow plumbing, and an auxiliary gas flow plumbing.

10. The electrospray ionization source of claim 9, wherein the electrospray ionization probe is configured to direct flow in the sheath gas flow plumbing coaxially to the electrospray emitter needle.

11. The electrospray ionization source of claim 9, wherein the electrospray ionization probe is configured to direct the flow in the auxiliary gas flow plumbing coaxially to the electrospray emitter needle.

12. The electrospray ionization source of claim 1, wherein the sheath gas inlet line is partially inserted into to the inlet line port.

13. The electrospray ionization source of claim 1, wherein the modified desolvation gas outlet line is partially inserted into to the outlet line port.

14. The electrospray ionization source of claim 1, wherein the sheath gas flows from the sheath gas inlet line through the container containing an organic solvent into the desolvation gas outlet line.

15. The electrospray ionization source of claim 1, wherein the container is surrounded by a second container.

16. The electrospray ionization source of claim 1, wherein the electrospray ionization source is capable of being connected to a liquid chromatographic system.

17. A method of characterizing a protein in a sample, comprising:
   supplying the sample to an inlet of an electrospray ionization source; wherein the electrospray ionization source comprises:
   a container having a cap, wherein the cap has an inlet line port and an outlet line port, wherein the container comprises an organic solvent and an acid, wherein a volume of said organic solvent is less than a volume of said acid;

a sheath gas inlet line for providing a sheath gas to the inlet line port; and a modified desolvation gas outlet line capable of connecting the outlet line port to a sheath gas inlet of an electrospray ionization probe;

generating ions of components of the protein in the sample at an outlet of the electrospray ionization source; and analyzing the ions using a mass spectrometer to identify the components of the protein to characterize the protein.

18. The method of claim 17, wherein the electrospray ionization source is connected to a liquid chromatographic system.

19. The method of claim 17, wherein the electrospray ionization probe is in a positive polarity mode.

20. The method of claim 17, wherein the electrospray ionization probe is in a negative polarity mode.

21. The method of claim 17, wherein characterizing the protein comprises conducting an intact mass analysis.

22. The method of claim 17, wherein characterizing the protein comprises conducting a peptide mapping analysis.

23. The method of claim 17, wherein the protein is an antibody.

24. The method of claim 17, wherein the electrospray ionization source provides an electrospray with a solvent flow rate of greater than about 5 µL/min.

25. A liquid chromatography mass spectrometry system, comprising:

a liquid chromatography device configured to direct a flow of a sample to an electrospray ionization source; wherein the electrospray ionization source comprises;

a container having a cap, wherein the cap has an inlet line port and an outlet line port, wherein the container comprises an organic solvent and an acid, wherein a volume of said organic solvent is less than a volume of said acid;

a sheath gas inlet line for providing a sheath gas to the inlet line port; and a modified desolvation gas outlet line capable of connecting the outlet line port to a sheath gas inlet of an electrospray ionization probe; and wherein the electrospray ionization source is configured to charge and desolvate the sample to form ions of components of the sample; and a mass spectrometry device configured to receive the ions and characterize mass to charge ratio of the ions.

* * * * *